US007884947B2

(12) United States Patent
De Lega et al.

(10) Patent No.: US 7,884,947 B2
(45) Date of Patent: ***Feb. 8, 2011

(54) INTERFEROMETRY FOR DETERMINING CHARACTERISTICS OF AN OBJECT SURFACE, WITH SPATIALLY COHERENT ILLUMINATION

(75) Inventors: Xavier Colonna De Lega, Middletown, CT (US); Peter De Groot, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 670 days.

This patent is subject to a terminal disclaimer.

(21) Appl. No.: 11/758,252

(22) Filed: Jun. 5, 2007

(65) Prior Publication Data

US 2008/0088849 A1    Apr. 17, 2008

Related U.S. Application Data

(63) Continuation-in-part of application No. 11/335,873, filed on Jan. 19, 2006, now Pat. No. 7,446,882, and a continuation-in-part of application No. 11/335,871, filed on Jan. 19, 2006, and a continuation-in-part of application No. 11/334,949, filed on Jan. 19, 2006, now Pat. No. 7,428,057.

(60) Provisional application No. 60/645,448, filed on Jan. 20, 2005.

(51) Int. Cl.
*G01B 11/02* (2006.01)
(52) U.S. Cl. ..................................... 356/511
(58) Field of Classification Search ................ 356/511, 356/495, 497, 512
See application file for complete search history.

(56) References Cited

U.S. PATENT DOCUMENTS

| | | | |
|---|---|---|---|
| 2,612,074 | A | 9/1952 | Mirau |
| 4,188,122 | A | 2/1980 | Massie et al. |
| 4,199,219 | A | 4/1980 | Suzuki et al. |

(Continued)

FOREIGN PATENT DOCUMENTS

DE        4108944        9/1992

(Continued)

OTHER PUBLICATIONS

Hamamatsu, "Mercury Xenon" catalogue listing, http://sales.hamamatsu.com/en/products/electron-tube-division/light-sources.php. Accessed via Internet Archive Wayback Machine for Jun. 25, 2004 at http://web.archive.org.*

(Continued)

*Primary Examiner*—Gregory J Toatley
*Assistant Examiner*—Scott M Richey
(74) *Attorney, Agent, or Firm*—Fish & Richardson P.C.

(57) ABSTRACT

Disclosed is an apparatus which includes: an interferometer configured to direct broadband spatially coherent test light to a test surface of a test object over a range of illumination angles and subsequently combine it with reference light to form an interference pattern, the test and reference light being derived from a common source; and multi-element detector; and one or more optics configured to direct at least a portion of the combined light to the detector so that different elements of the detector correspond to different illumination angles of a region of the test surface illuminated by the test light.

47 Claims, 8 Drawing Sheets

U.S. PATENT DOCUMENTS

| | | |
|---|---|---|
| 4,340,306 A | 7/1982 | Balasubramanian |
| 4,355,903 A | 10/1982 | Sandercock |
| 4,523,846 A | 6/1985 | Breckinridge et al. |
| 4,576,479 A | 3/1986 | Downs |
| 4,583,858 A | 4/1986 | Lebling et al. |
| 4,618,262 A | 10/1986 | Maydan et al. |
| 4,639,139 A | 1/1987 | Wyant et al. |
| 4,660,980 A | 4/1987 | Takabayashi et al. |
| 4,710,642 A | 12/1987 | McNeil |
| 4,806,018 A | 2/1989 | Falk |
| 4,818,110 A | 4/1989 | Davidson |
| 4,869,593 A | 9/1989 | Biegen |
| 4,923,301 A | 5/1990 | White |
| 4,948,253 A | 8/1990 | Biegen |
| 4,964,726 A | 10/1990 | Kleinknecht et al. |
| 4,999,014 A | 3/1991 | Gold et al. |
| 5,008,889 A * | 4/1991 | Wilson ................. 372/32 |
| 5,042,949 A | 8/1991 | Greenberg et al. |
| 5,042,951 A | 8/1991 | Gold et al. |
| 5,073,018 A | 12/1991 | Kind et al. |
| 5,112,129 A | 5/1992 | Davidson et al. |
| 5,129,724 A | 7/1992 | Brophy et al. |
| 5,133,601 A | 7/1992 | Cohen et al. |
| 5,135,307 A | 8/1992 | De Groot et al. |
| 5,153,669 A | 10/1992 | DeGroot |
| 5,164,790 A | 11/1992 | McNeil et al. |
| 5,166,751 A | 11/1992 | Massig |
| 5,173,746 A | 12/1992 | Brophy |
| 5,194,918 A | 3/1993 | Kino et al. |
| 5,241,369 A | 8/1993 | McNeil et al. |
| 5,301,010 A | 4/1994 | Jones et al. |
| 5,355,221 A | 10/1994 | Cohen et al. |
| 5,384,717 A | 1/1995 | Ebenstein |
| 5,386,119 A | 1/1995 | Ledger |
| 5,390,023 A | 2/1995 | Biegen |
| 5,398,113 A | 3/1995 | De Groot |
| 5,402,234 A | 3/1995 | Deck |
| 5,459,564 A | 10/1995 | Chivers |
| 5,471,303 A | 11/1995 | Ai et al. |
| 5,481,811 A | 1/1996 | Smith |
| 5,483,064 A | 1/1996 | Frey et al. |
| 5,539,571 A | 7/1996 | Cabib et al. |
| 5,543,841 A | 8/1996 | Kanamori |
| 5,555,471 A | 9/1996 | Xu et al. |
| 5,587,792 A | 12/1996 | Nishizawa et al. |
| 5,589,938 A | 12/1996 | Deck |
| 5,602,643 A | 2/1997 | Barrett |
| 5,633,714 A | 5/1997 | Nyyssonen |
| 5,640,270 A | 6/1997 | Aziz et al. |
| 5,703,692 A | 12/1997 | McNeil et al. |
| 5,757,502 A | 5/1998 | Weling |
| 5,774,224 A | 6/1998 | Kerstens |
| 5,777,736 A * | 7/1998 | Horton ................. 356/456 |
| 5,777,740 A | 7/1998 | Lacey et al. |
| 5,777,742 A | 7/1998 | Marron |
| 5,784,164 A | 7/1998 | Deck et al. |
| 5,856,871 A | 1/1999 | Cabib et al. |
| 5,867,276 A | 2/1999 | McNeil et al. |
| 5,880,838 A | 3/1999 | Marx et al. |
| 5,900,633 A | 5/1999 | Solomon et al. |
| 5,912,741 A | 6/1999 | Carter et al. |
| 5,923,423 A | 7/1999 | Sawarti et al. |
| 5,943,134 A | 8/1999 | Yamaguchi et al. |
| 5,953,124 A | 9/1999 | Deck |
| 5,956,141 A | 9/1999 | Hayashi |
| 5,959,735 A | 9/1999 | Maris et al. |
| 5,963,329 A | 10/1999 | Conrad et al. |
| 6,028,670 A | 2/2000 | Deck |
| 6,160,621 A | 12/2000 | Perry et al. |
| 6,172,452 B1 | 1/2001 | Itaya et al. |
| 6,242,739 B1 | 6/2001 | Cherkassky |
| 6,249,351 B1 | 6/2001 | de Groot |
| H1972 H | 7/2001 | Inoue |
| 6,259,521 B1 | 7/2001 | Miller et al. |
| 6,275,297 B1 | 8/2001 | Zalicki |
| 6,377,349 B1 | 4/2002 | Fercher |
| 6,381,009 B1 | 4/2002 | McGahan |
| 6,392,749 B1 | 5/2002 | Meeks et al. |
| 6,417,109 B1 | 7/2002 | Jordan et al. |
| 6,429,943 B1 | 8/2002 | Opsal et al. |
| 6,449,048 B1 | 9/2002 | Olszak |
| 6,449,066 B1 | 9/2002 | Arns et al. |
| 6,483,580 B1 | 11/2002 | Xu et al. |
| 6,500,591 B1 | 12/2002 | Adams |
| 6,507,405 B1 | 1/2003 | Grek et al. |
| 6,525,825 B2 | 2/2003 | de Groot |
| 6,545,761 B1 | 4/2003 | Aziz et al. |
| 6,545,763 B1 | 4/2003 | Kim et al. |
| 6,590,656 B2 | 7/2003 | Xu et al. |
| 6,597,460 B2 | 7/2003 | Groot et al. |
| 6,611,330 B2 | 8/2003 | Lee et al. |
| 6,624,894 B2 | 9/2003 | Olszak et al. |
| 6,633,389 B1 | 10/2003 | Poris et al. |
| 6,633,831 B2 | 10/2003 | Nikoonahad et al. |
| 6,636,322 B1 | 10/2003 | Terashita |
| 6,690,473 B1 * | 2/2004 | Stanke et al. ................. 356/601 |
| 6,694,284 B1 | 2/2004 | Nikoonahad et al. |
| 6,714,307 B2 | 3/2004 | De Groot et al. |
| 6,721,094 B1 | 4/2004 | Sinclair et al. |
| 6,741,360 B2 | 5/2004 | D'Agraives et al. |
| 6,775,006 B2 | 8/2004 | De Groot et al. |
| 6,775,009 B2 | 8/2004 | Hill |
| 6,798,511 B1 | 9/2004 | Zhan et al. |
| 6,822,745 B2 | 11/2004 | De Groot et al. |
| 6,856,384 B1 | 2/2005 | Rovira |
| 6,885,460 B2 * | 4/2005 | Morita ................. 356/514 |
| 6,888,638 B1 | 5/2005 | Hill |
| 6,891,627 B1 | 5/2005 | Levy et al. |
| 6,909,509 B2 | 6/2005 | DeGroot |
| 6,925,860 B1 | 8/2005 | Poris et al. |
| 6,940,604 B2 | 9/2005 | Jung et al. |
| 6,956,658 B2 | 10/2005 | Meeks et al. |
| 6,956,660 B2 | 10/2005 | Meeks et al. |
| 6,985,232 B2 | 1/2006 | Sezginer |
| 6,989,905 B2 | 1/2006 | De Groot |
| 6,999,180 B1 | 2/2006 | Janik et al. |
| 7,012,700 B2 | 3/2006 | de Groot et al. |
| 7,018,271 B2 | 3/2006 | Wiswesser et al. |
| 7,038,850 B2 | 5/2006 | Chang et al. |
| 7,046,371 B2 | 5/2006 | De Lega et al. |
| 7,061,623 B2 * | 6/2006 | Davidson ................. 356/497 |
| 7,068,376 B2 | 6/2006 | De Groot |
| 7,088,451 B2 | 8/2006 | Sezginer |
| 7,102,761 B2 | 9/2006 | De Lega et al. |
| 7,106,454 B2 | 9/2006 | De Groot et al. |
| 7,119,909 B2 | 10/2006 | Unruh et al. |
| 7,139,081 B2 | 11/2006 | De Groot |
| 7,139,083 B2 | 11/2006 | Fielden et al. |
| 7,142,311 B2 | 11/2006 | De Lega |
| 7,177,030 B2 | 2/2007 | Leizerson |
| 7,205,518 B2 | 4/2007 | Neuvonen |
| 7,239,398 B2 | 7/2007 | De Groot et al. |
| 7,271,918 B2 | 9/2007 | De Groot et al. |
| 7,283,248 B2 | 10/2007 | Hill |
| 7,289,225 B2 | 10/2007 | De Groot |
| 7,298,494 B2 | 11/2007 | De Groot |
| 7,304,747 B2 | 12/2007 | De Lega |
| 7,315,382 B2 | 1/2008 | De Groot |
| 7,324,210 B2 | 1/2008 | De Groot et al. |
| 7,324,214 B2 | 1/2008 | De Groot et al. |
| 6,741,357 B2 | 5/2008 | Wang et al. |
| 7,428,057 B2 * | 9/2008 | De Lega et al. ............. 356/511 |
| 7,446,882 B2 * | 11/2008 | De Lega et al. ............. 356/512 |
| 2002/0015146 A1 | 2/2002 | Meeks et al. |

| | | | |
|---|---|---|---|
| 2002/0135775 A1 | 9/2002 | de Groot et al. |
| 2002/0148955 A1 | 10/2002 | Hill |
| 2002/0196450 A1 | 12/2002 | Olszak et al. |
| 2003/0011784 A1 | 1/2003 | de Groot et al. |
| 2003/0048458 A1 | 3/2003 | Mieher et al. |
| 2003/0075721 A1 | 4/2003 | Li |
| 2003/0112444 A1 | 6/2003 | Yang et al. |
| 2003/0137671 A1 | 7/2003 | De Groot et al. |
| 2003/0197871 A1 | 10/2003 | De Groot |
| 2004/0027576 A1 | 2/2004 | De Groot et al. |
| 2004/0075843 A1 | 4/2004 | Marron et al. |
| 2004/0085544 A1 | 5/2004 | de Groot et al. |
| 2004/0185582 A1 | 9/2004 | Kueny |
| 2004/0189999 A1 | 9/2004 | de Groot et al. |
| 2004/0233442 A1 | 11/2004 | Mieher et al. |
| 2004/0233444 A1 | 11/2004 | Mieher et al. |
| 2004/0246493 A1 | 12/2004 | Kim et al. |
| 2005/0024773 A1 | 2/2005 | Lille |
| 2005/0057757 A1 | 3/2005 | de Lega et al. |
| 2005/0068540 A1 | 3/2005 | de Groot et al. |
| 2005/0073692 A1 | 4/2005 | de Groot et al. |
| 2005/0078318 A1 | 4/2005 | de Groot |
| 2005/0078319 A1 | 4/2005 | de Groot |
| 2005/0088663 A1 | 4/2005 | de Groot et al. |
| 2005/0146727 A1 | 7/2005 | Hill |
| 2005/0179911 A1 | 8/2005 | Boomgarden et al. |
| 2005/0225769 A1 | 10/2005 | Bankhead et al. |
| 2005/0237534 A1 | 10/2005 | Deck |
| 2005/0237537 A1 | 10/2005 | Leizerson et al. |
| 2006/0012582 A1 | 1/2006 | de Lega |
| 2006/0072104 A1 | 4/2006 | Engel et al. |
| 2006/0119841 A1 | 6/2006 | Saunders et al. |
| 2006/0158657 A1 | 7/2006 | de Lega et al. |
| 2006/0158658 A1 | 7/2006 | Colonna de Lega et al. |
| 2006/0158659 A1 | 7/2006 | Colonna de Lega et al. |
| 2006/0170932 A1 | 8/2006 | Hayashi et al. |
| 2006/0187465 A1 | 8/2006 | De Groot |
| 2006/0262321 A1 | 11/2006 | De Groot |
| 2007/0008551 A1 | 1/2007 | Tang |
| 2007/0046953 A1 | 3/2007 | de Groot et al. |
| 2007/0081167 A1 | 4/2007 | De Groot |
| 2007/0086013 A1 | 4/2007 | De Lega et al. |
| 2007/0091317 A1 | 4/2007 | Freischlad et al. |
| 2007/0091318 A1 | 4/2007 | Freishlad et al. |
| 2007/0091940 A1 | 4/2007 | Jameson |
| 2007/0097380 A1 | 5/2007 | De Groot et al. |
| 2007/0127036 A1 | 6/2007 | Liao et al. |
| 2007/0139656 A1 | 6/2007 | Wan |
| 2007/0247637 A1 | 10/2007 | De Groot |
| 2008/0018901 A1 | 1/2008 | de Groot |
| 2008/0088849 A1 | 4/2008 | de Lega et al. |
| 2008/0174784 A1 | 7/2008 | de Lega et al. |

FOREIGN PATENT DOCUMENTS

| | | |
|---|---|---|
| DE | 4309056 | 9/1994 |
| EP | 0 397 388 A2 | 11/1990 |
| EP | 0 549 166 A2 | 6/1993 |
| EP | 0 617 255 A1 | 9/1994 |
| EP | 0 929 094 A2 | 7/1999 |
| GB | 2385417 | 8/2003 |
| JP | 8327327 | 12/1996 |
| JP | 09-218016 | 8/1997 |
| JP | 2000121317 | 4/2000 |
| JP | 2000-180124 | 6/2000 |
| JP | 2001-272603 | 10/2001 |
| JP | 2001-141652 | 5/2009 |
| KR | 20000061037 | 10/2000 |
| WO | WO 93/24805 | 12/1993 |
| WO | WO 94/00733 | 1/1994 |
| WO | WO 95/09343 | 4/1995 |
| WO | WO 97/44633 | 11/1997 |
| WO | WO 02/082008 | 10/2002 |
| WO | WO 03/036229 | 5/2003 |
| WO | WO 03/062802 | 7/2003 |
| WO | WO 2004/023071 | 3/2004 |
| WO | WO 2005/029192 | 3/2005 |

OTHER PUBLICATIONS

Abdulhalim, "Spectroscopic interference microscopy technique for measurement of layer parameters", Meas. Sci. Technol., vol. 12, pp. 1996-2001 (2001).

Biegen, "Determination of the Phase Change on Reflection from Two-beam Interference," Optics Letters, 19:21:1690-1692, Nov. 1, 1994.

Bishop, et al., "Grating line shape characterization using scatterometry," SPIE 1545, 64-73 (1991).

Chim, S. S. C. and Kino, G. S., "Three-Dimensional Image Realization in Interference Microscopy", Applied Optics, May 10, 1992, vol. 31, No. 14.

Creath, "Step height measurement using two-wavelength phase-shifting interferometry", Applied Optics, vol. 26, No. 14, pp. 2810-2816 (Jul. 15, 1987).

Danielson et al., "Absolute Optical Ranging Using Low Coherence Interferometry," Applied Optics, 30:21:2975-2979, Jul. 20, 1991.

de Groot et al., "Angle-resolved three-dimensional analysis of surface films by coherence scanning interferometry", Optics Letters, vol. 32, No. 12, pp. 1638-1640 (Jun. 15, 2007).

de Groot et al.; "Three-dimensional imaging by sub-Nyquist sampling of white-light interfergrams"; Optics Letters vol. 18, No. 17; pp. 1462-1464, Sep. 1, 1993.

de Groot, "Extending the unambiguous range of two-color interferometers", Applied Optics, vol. 33, No. 25, pp. 5948-5953 (Sep. 1, 1994).

de Groot, "Three-color laser-diode interferometer", Applied Optics, vol. 30, No. 25, pp. 3612-3616 (Sep. 1, 1991).

de Groot, P., "Phase-shift calibration errors in interometers with spherical Fizeau cavities," Applied Optics, vol. 34:16, pp. 2856-2863 (Jun. 1, 1995).

de Lega, X., et al., "Optical topography measurement of patterned wafers," American Institute of Physics Conference Proceedings, vol. 788, pp. 432-436 (2005).

Debnath, S.K., et al., "Spectrally resolved phase-shifting interferometry of transparent thin films: sensitivity of thickness measurements," Appl. Opt. 45, 34 8636-8640 (2006).

Deck et al., "Two-color light-emitting-diode source for high-precision phase-shifting interferometry", Optics Letters, vol. 18, No. 22, pp. 1899-1901 (Nov. 15, 1993).

Gale et al., "Linnik microscope imaging of integrated circuit structures", Applied Optics vol. 35, No. 1, pp. 131-148 (Jan. 1, 1996).

Ghiglia et al., "Quality-Guided Path Following", Two-Dimensional Phase Unwrapping—Theory, Algorithms and Software, John Wiley & Sons publishers, ISBN 0-471-24935-1, pp. 122-136 (1998).

Kleinknecht, et al., "Linewidth measurement on IC masks and wafers by grating test patterns," Appl. Opt. 19(4), 523-533 (1980).

Kohlhaas, A. Fromchen, C. and Brinkmeyer, E., "High-Resolution OCDR for Testing Integrated-Optical Waveguides: Dispersion-Corrupted Experimental Data Corrected by a Numerical Algorithm", Journal of Lightwave Technology, Nov. 1991, vol. 9, No. 11.

Naqvi, et al., "Linewidth measurement of gratings on photomasks: a simple technique," Appl. Opt., 31(10), 1377-1384 (1992).

Novak et al., "Template-based software for accurate MEMS characterization", Proceedings of SPIE, Fol. 4980, pp. 75-80 (2003).

Onodera et al., "Two-wavelength interferometry that uses a Fourier-transform method", Applied Optics, vol. 37, No. 34, pp. 7988-7994 (Dec. 1, 1998).

Peng, S.T., et al., "Theory of Periodic Dielect Waveguides," IEEE Trans Microwave Theory and Technique MTT-23(1), 123-133 (1975).

Pfortner et al., "Red-green-blue interferometer for the metrology of discontinuous structures", Applied Optics, vol. 42, No. 4, pp. 667-673 (Feb. 1, 2003).

Raymond, C.J., "Scatterometry for Semiconductor Metrology," in Handbook of silicon semiconductor metrology, A.J. Deibold, Ed. (Marcel Dekker, Inc., New York 2001).

Raymond, et al., "Scatterometry for CD measurements of etched structures," SPIE 2725, 720-728 (1996).

Schmit, J. et al., "Extended averaging technique for derivation of error-compensating algorithms in phase-shifting interferometry," Applied Optics, vol. 34:19, pp. 3610-3619 (Jul. 1, 1995).

Sheppard et al., "Effect of numerical aperture on interference fringe spacing", Applied Optics, vol. 34, No. 22, pp. 4731-4734 (Aug. 1, 1995).

Tzannes et al., Measurement of the modulation transfer function of infrared cameras, Optical Engineering, vol. 34, No. 6, pp. 1808-1817 (Jun. 1995). cited by other.

Wyant, "Phase shifting interferometry" (1998).

Youngquist, R. C. Carr, S. and Davies, D. E. N., "Optical Coherence-Domain Reflectometry: a New Optical Evaluation Technique", Optical Letters, Mar. 1987, vol. 12, No. 3.

Zhan, Q., et al., "Measurement of surface features beyond the diffraction limit with an imaging ellipsometer," Opt. Lett. 27, 821-823 (2002).

PCT Search Report dated Jun. 10, 2008.

The International Search Report; International Appln. No. PCT/US08/65863, filed May 6, 2008.

C. Akcay et al., "Spectral shaping to improve the point spread function in optical coherence tomography", Optics Letters, vol. 28 No. 20, pp. 1921-1923 (Oct. 15, 2003).

R.M.A. Azzam et al., "Reflection and Transmission of Polarized Light by Stratified Planar Structures", Ellipsometry and Polarized Light, Elsevier Science B.V. ISBN 0 444 87016 4 (Paperback) pp. 267-363 (1987).

R.M.A. Azzam et al, "Ellipsometric function of a film-substrate system: Applications to the design of reflection-type optical devices and to ellipsometry", Journal of the Optical Society of America, vol. 5, No. 3, pp. 252-260.

M. Bashkansky et al., "Signal Processing for Improving Field Cross-correlation Function in Optical Coherence Tomography", Supplement to Optics & Photonics News, 9(5) (May 1998).

Berman et al., "Review of in Situ & In-line Detection for CMP Applications", Semiconductor Fabtech—$8^{th}$ Edition, pp. 267-274.

A. Bosseboeuf et al., "Application of microscopic interferometry techniques in the MEMS field", Proceedings of SPIE, vol. 5145, pp. 1-16 (2003).

M. Davidson et al., "An Application of Interference Microscopy to Integrated Circuit Inspection and metrology", Proceedings SPIE, vol. 775, pp. 233-247 (1987).

T. Dresel et al., "Three-dimensional sensing of rough surfaces by coherence radar", Applied Optics, vol. 31, No. 7, pp. 919-925 (Mar. 1, 1992).

J.E. Greivenkamp, "Generalized data reduction for heterodyne interferometry", Optical Engineering., vol. 23 No. 4, pp. 350-352 (Jul./Aug. 1984)

P. de Groot et al., "Signal modeling for low coherence height-scanning interference microscopy", Applied Optics, vol. 43 No. 25, pp. 4821-4830 (Sep. 1, 2004).

P. de Groot, "Derivation of algorithms for phase-shifting interferometry using the concept of a data-sampling window", Appl. Opt., 34(22), p. 4723-4730 (1995).

P. de Groot et al., "Signal modeling for modern interference microscopes", SPIE Proceedings, 5457-4 (2004).

Peter de Groot et al., "Determination of fringe order in white-light interference microscopy", Appl. Opt., 41(22) pp. 4571-4578 (2002).

Feke, Gilbert D. et al., "Interferometric back focal plane microellipsometry", Applied Optics, vol. 37, No. 10, pp. 1796-1802 (Apr. 1, 1998).

P.A. Flournoy et al., "White-light interferometric thickness gauge", Appl. Opt., 11(9), pp. 1907-1915 (1972).

G. Hausler et al., "Coherence Radar and Spectral Radar—New Tools for Dermatological Diagnosis", Journal of Biomedical Optics, vol. 3, No. 1, pp. 21-31 (Jan. 1998).

E. Hecht, "Basics of Coherence Theory", Optics, Second Edition, Addison Wesley, pp. 516-517 (1987).

R.D. Holmes et al., "Scanning microellipsometry for extraction of true topograpy", Electronics Letters, vol. 31, No. 5, pp. 358-359 (Mar. 2, 1995).

Kim, Seung-Woo et al., "Thickness-profile measurement of transparent thin-film layers by white-light scanning interferometry", Applied Optics, vol. 38, No. 28, pp. 5968-5973 (Oct. 1, 1999).

Kino, Gordon S. et al., "Mirau correlation microscope", Applied Optics, vol. 29, No. 26, pp. 3775-3783 (Sep. 10, 1990).

Kieran G. Larkin, "Efficient nonlinear algorithm for envelope detection in white light interferometry", Journal of the Optical Society of America A, vol. 13, No. 4, pp. 832-843 (1996).

Kujawinska, Malgorzata, "Spatial Phase Measurement Methods", Interferogram Analysis: Digital Fringe Pattern Measurement Techniques, IOP Publishing Ltd. 1993, pp. 141-193.

Lee et al., "Profilometry with a coherence scanning microscope", Appl. Opt., 29(26), pp. 3784-3788 (1990).

I. Lee-Bennett, "Advances in non-contacting (2004) surface metrology", OF&T Workshop, papter OTuC1 (2004).

K. Leonhardt et al., "Micro-Ellipso-Height-Profilometry", Optics Communications, vol. 80, No. 3, 4, pp. 205-509 (Jan. 1, 1991).

Y. Liu et al., "Common path interferometric microellipsometry", SPIE, vol. 2782, pp. 635-645 (1996).

Lyakin et al., "The interferometric system with resolution better than coherence determination length for determination of geometrical thickness and refractive index of a layer object", Proceedings of the SPIE—The International Society for Optical Engineering SPIE-INT. Soc. Opt. Eng USA, vol. 4956, pp. 163-169 (Jul. 2003).

C.J. Morgan, "Least-Squares estimation in phase-measurement interferometry", Optics Letters, 7(8), pp. 368-370 (1982).

Ngoi et al., "Phase-shifting interferometry immune to vibration", Applied Optics, vol. 40, No. 19, pp. 3211-3214 (2001).

A.V. Oppenheim et al., "10.3: The time-dependent Fourier Transform", Discrete-Time Signal Processing, $2^{nd}$ Edition, pp. 714-722 (Prentice Hall, New Jersey, 1999).

M.C. Park et al., "Direct quadratic polynomial fitting for fringe peak detection of white light scanning interferograms", Optical Engineering, vol. 39, No. 4, pp. 952-959 (2000).

S. Pettigrand et al., "Mesures 3D de topographies a l'echelle (sub)micrometrique par microscopie optique interferometrique", Proc. Club CMOI, Methodes et Techniques Optiques pour l'Industrie, (2002).

M. Pluta, "Advanced light microscopy", vol. 3, PWN—Polish Scientific Publishers (Elsevier, Amsterdam), pp. 265-271 (1993).

W.H. Press et al., "Linear Correlation", Numerical Recipes in C, Cambridge University Press, $2^{nd}$ Edition, pp. 636-639 (1992).

Rosencwaig, Allan et al., "Beam profile reflectometry: A new technique for dielectric film measurements", Applied Physics Letters, vol. 60, No. 11, pp. 1301-1303 (Mar. 16, 1992).

P. Sandoz et al., "Optical implementation of frequency domain analysis for white light interferometry", Proceedings SPIE, vol. 2545, pp. 221-228 (Jun. 1995).

P. Sandoz et al., "High-resolution profilometry by using phase calculation algorithms for spectroscopic analysis of white-light interferograms", Journal of Modern Optics, vol. 43, No. 4, pp. 701-708 (1996).

Sandoz, Patrick "Wavelet transform as a processing tool in white-light interferometry", Optics Letters, vol. 22, No. 14, pp. 1065-1067 (Jul. 15, 1997).

P. Sandoz et al., "Processing of white light correlograms: simultaneous phase and envelope measurements by wavelet transformation", SPIE, vol. 3098, pp. 73-82 (1997).

U. Schnell et al., "Dispersive white-light interferometry for absolute distance measurement with dielectric multilayer systems on the target", Optics Letters, vol. 21, No. 7, pp. 528-530 (Apr. 1996).

J. Schwider et al., "Dispersive interferometric profilometer", Optics Letters, vol. 19, No. 13, pp. 995-997 (Jul. 1994).

C.W. See et al., "Scanning optical microellipsometer for pure surface profiling", Applied Optics, vol. 35, No. 34, pp. 6663-6668 (Dec. 1, 1996).

Shatalin, S.V. et al., "Reflection conoscopy and micro-ellipsometry of isotropic thin film structures", Journal of Microscopy, vol. 179, Part 3, pp. 241-252 (Sep. 1995).

M. Totzeck,"Numerical simulation of high-NA quantitative polarization microscopy and corresponding near-fields", Optik, vol. 112, No. 9, pp. 399-406 (2001).

R. Tripathi et al., "Spectral shaping for non-Gaussian source spectra in optical coherence tomography", *Optics Letters*, vol. 27, No. 6, pp. 406-408 (Mar. 15, 2002).

D. Willenborg et al, "A novel micro-spot dielectric film thickness measurement system", *SPIE*, vol. 1594, pp. 322-333 (1991).

International Search Report for International Application No. PCT/US2006/001740 dated Jun. 6, 2006 by Authorized Officer Sibylle Schubert-Püschel.

Encyclopedia of Laser Physics and Technology, http://www.rp-photonics.com/coherence.html.

Encyclopedia of Laser Physics and Technology, http://www.rp-photonics.com/single_mode_fibers.html.

Encyclopedia of Laser Physics and Technology, http://www.rp-photonics.com/photonic_crystal_fibers.html.

Encyclopedia of Laser Physics and Technology, http://www.rp-photonics.com/supercontinuum_generation.html.

George O. Reynolds et al., "The New Physical Optics Notebook: Tutorials in Fourier Optics", SPIE—The International Society for Optical Engineering and American Institute of Physics (1989).

US 7,151,607, 12/2008, De Groot et al. (withdrawn)

* cited by examiner

— SIGNAL INTENSITY

— SPECTRAL MAGNITUDE
----- SPECTRAL PHASE

INTERFEROMETRY FOR DETERMINING CHARACTERISTICS OF AN OBJECT SURFACE, WITH SPATIALLY COHERENT ILLUMINATION

CROSS-REFERENCE TO RELATED APPLICATIONS

This application is a continuation-in-part and claims benefit under 35 USC §120 of the following U.S. applications: U.S. patent application Ser. No. 11/335,873, entitled "INTERFEROMETER FOR DETERMINING CHARACTERISTICS OF AN OBJECT SURFACE," and filed Jan. 19, 2006, now U.S. Pat. No. 7,446,882 U.S. patent application Ser. No. 11/335,871, entitled "INTERFEROMETER WITH MULTIPLE MODES OF OPERATION FOR DETERMINING CHARACTERISTICS OF AN OBJECT SURFACE," and filed Jan. 19, 2006, and U.S. patent application Ser. No. 11/334,949, entitled "INTERFEROMETER FOR DETERMINING CHARACTERISTICS OF AN OBJECT SURFACE, INCLUDING PROCESSING AND CALIBRATION," and filed Jan. 19, 2006, now U.S. Pat. No. 7,428,057 each of which is in incorporated herein by reference. Each of these references claim priority under 35 U.S.C. §119(e) to U.S. Provisional Patent Application Ser. No. 60/645,448, entitled "INTERFEROMETER FOR DETERMINING CHARACTERISTICS OF AN OBJECT SURFACE," and filed Jan. 20, 2005, the contents of which is incorporated herein by reference.

BACKGROUND

The invention relates to interferometry.

Interferometric techniques are commonly used to measure the profile of a surface of an object. To do so, an interferometer combines a measurement wavefront reflected from the surface of interest with a reference wavefront reflected from a reference surface to produce an interferogram. Fringes in the interferogram are indicative of spatial variations between the surface of interest and the reference surface.

A scanning interferometer scans the optical path length difference (OPD) between the reference and measurement legs of the interferometer over a range comparable to, or larger than, the coherence length of the interfering wavefronts, to produce a scanning interferometry signal for each camera pixel used to measure the interferogram. A limited coherence length can be produced, for example, by using a white-light source, which is referred to as scanning white light interferometry (SWLI). A typical scanning white light interferometry (SWLI) signal is a few fringes localized near the zero optical path difference (OPD) position. The signal is typically characterized by a sinusoidal carrier modulation (the "fringes") with bell-shaped fringe-contrast envelope. The conventional idea underlying SWLI metrology is to make use of the localization of the fringes to measure surface profiles.

SWLI processing techniques include two principle trends. The first approach is to locate the peak or center of the envelope, assuming that this position corresponds to the zero optical path difference (OPD) of two-beam interfrometer for which one beam reflects from the object surface. The second approach is to transform the signal into the frequency domain and calculate the rate of change of phase with wavelength, assuming that an essentially linear slope is directly proportional to object position. See, for example, U.S. Pat. No. 5,398,113 to Peter de Groot. This latter approach is referred to as Frequency Domain Analysis (FDA).

Scanning interferometry can be used to measure surface topography and/or other characteristics of objects having complex surface structures, such as thin film(s), discrete structures of dissimilar materials, or discrete structures that are underresolved by the optical resolution of an interference microscope. Such measurements are relevant to the characterization of flat panel display components, semiconductor wafer metrology, and in-situ thin film and dissimilar materials analysis. See, e.g., U.S. Patent Publication No. US-2004-0189999-A1 by Peter de Groot et al. entitled "Profiling Complex Surface Structures Using Scanning Interferometry" and published on Sep. 30, 2004, the contents of which are incorporated herein by reference, and U.S. Patent Publication No. US-2004-0085544-A1 by Peter de Groot entitled "Interferometry Method for Ellipsometry, Reflectometry, and Scatterometry Measurements, Including Characterization of This Film Structures" and published on May 6, 2004, the contents of which are incorporated herein by reference.

Other techniques for optically determining information about an object include ellipsometry and reflectometry. Ellipsometry determines complex reflectivity of a surface when illuminated at an oblique angel, e.g. 60°, sometimes with a variable angle or with multiple wavelengths. To achieve greater resolution than is readily achievable in a conventional ellipsometer, microellipsometers measure phase and/or intensity distributions in the back focal plane of the objective, also known as the pupil plane, where the various illumination angles are mapped into field positions. Such devices are modernizations of traditional polarization microscopes or "conoscopes," linked historically to crystallography and mineralogy, which employs crossed polarizers and a Bertrand lens to analyze the pupil plane birefringent materials.

Conventional techniques used for thin film characterization (e.g., ellipsometry and reflectometry) rely on the fact that the complex reflectivity of an unknown optical interface depends both on its intrinsic characteristics (material properties and thickness of individual layers) and on three properties of the light that is used for measuring the reflectivity: wavelength, angle of incidence, and polarization state. In practice, characterization instruments record reflectivity fluctuations resulting from varying these parameters over known ranges. Optimization procedures such as least-squares fits are then used to get estimates for the unknown parameters by minimizing the difference between measured reflectivity data and a reflectivity function derived from a model of the optical structure.

SUMMARY

In at least one embodiment, an interferometry method and apparatus is disclosed that produces angularly resolved interference signals from a test surface over a range of wavelengths. The information related to each wavelength may be extracted mathematically or in hardware. Furthermore, the optical hardware for obtaining the angularly resolved interference signals from the test surface is interchangeable with optical hardware useful for other surface characterization tasks, such as conventional interferometric surface profiling. Accordingly, an interferometry system is disclosed that is capable of operating in an ellipsometry mode for providing complex reflectivity information of the test surface for a range of angles, wavelengths, and polarizations, and a profiling mode for providing information about the test surface over a range of test surface locations.

We now summarize various aspects and features of the invention.

In general, in one aspect an apparatus includes: an interferometer configured to direct broadband spatially coherent test light to a test surface of a test object over a range of illumination angles and subsequently combine it with reference light to form an interference pattern, the test and reference light being derived from a common source; a multi-element detector; and one or more optics configured to direct at least a portion of the combined light to the detector so that different elements of the detector correspond to different illumination angles of a region of the test surface illuminated by the test light.

In some embodiments the apparatus includes the common source. The common source may be a broadband spatially coherent source. For example, in some embodiments the broadband source is a source spanning more than 50 nm at full width half maximum, more than 100 nm at full width half maximum, more than 500 nm at full width half maximum, or more than 1000 nm at full width half maximum.

In some embodiments the interferometer includes an interference objective having a pupil plane, and where the one or more optics image the interference pattern at the pupil plane to the multi-element detector.

In some embodiments input light is directed from the common source to the pupil plane. The input light directed to the pupil plane may be spatially coherent at the pupil plane. For example, the common source may output a beam having a waist, and the waist of the beam imaged to the pupil plain. A field stop may be positioned to define the spatial extent of the test light on the test surface.

In some embodiments, the interference objective is configured to focus the test light to a test spot at the test surface. For example, the width of the test spot may be about equal to the width of a diffraction spot of the interference objective at the test surface, about 150% or less of the width of a diffraction spot of the interference objective, or about 200% or less of the width of a diffraction spot of the interference objective. The numerical aperture of the interference objective may be greater than 0.7 or 0.0. In some embodiments, the width of the test spot is about 1 µm or less.

In some embodiments, the common source includes a light source optically coupled to an optical fiber configured to provide spatially coherent output light. For example, in various embodiments the light source includes one or more of: a lamp element, a laser, a light emitting diode, a light emitting diode array.

In some embodiments, the optical fiber includes a single mode fiber and/or a photonic bandgap fiber.

In some embodiments the optical fiber includes an optically nonlinear material. For example, in some embodiments, during operation, the fiber interacts with light from the light source propagating along the fiber to provide output light with a broader spectral range than the light source.

In some embodiments, the common source includes a resonant cavity configured to provide spatially coherent output light.

In some embodiments, the apparatus includes an optical element configured to operate selectively to reduce the spatial coherence of the test light.

In some embodiments the apparatus includes an electronic processor coupled to the detector. The electronic processor is configured to process information measured by the detector to determine information about the test object. In some embodiments, the test object includes one or more layers on a substrate.

In some embodiments the electronic processor extracts angularly resolved reflectivity information about the test surface from the detector measurement, and determines the information about the test object based on the angularly resolved information. For example, the apparatus may include a translation stage configured to adjust the relative optical path length between the test and reference light when they form the interference pattern. The electronic processor may be configured to analyze an interference intensity signal measured at each of multiple locations across the detector and produced by scanning the translation stage. In some embodiments, the electronic processor is configured, in a first mode, to determine the correspondence between the different regions of the detector and the different illumination angles of the test surface by the test light based on the frequency of the intensity signal at different locations on the detector. In some embodiments, the electronic processor is configured, in a first mode, to extract angularly resolved and wavelength-resolved information about the test surface based on the intensity signals measured across the detector.

In some embodiments the electronic processor is configured to determine the information about the test object based on a comparison between data based on the information measured by the detector and a model for the test object. For example, in some embodiments, the model provides an estimate for the measured information as a function of one or more parameters for the test object, and where the comparison selects values for the one or more parameters to optimize the fit between the measured information and that provided by the model.

In some embodiments, the electronic processor stores calibration information about the optical properties of the interferometer and uses the calibration information and the information measured by the detector to determine the information about the test object.

In some embodiments, the translation stage is configured to vary the optical path length over a range larger than a coherence length for the common source.

In some embodiments, the one or more optics are configured to direct at least a portion of the combined light to the detector so that different elements of the detector correspond to different locations on the region of the test surface illuminated by the test light.

In some embodiments, the electronic processor is configured, in a second mode, to process information measured by the different elements of the detector corresponding to different locations on the region of the test surface illuminated by the test light to determine information about a test object having the test surface.

In some embodiments, the electronic processor is configured to use information derived in one mode of operation to assist in determining further information about the test object when using another mode of operation.

In another aspect, a method includes: directing broadband spatially coherent test light to a test surface of a test object over a range of illumination angles and subsequently combining it with reference light to form an interference pattern, the test and reference light being derived from a common source; and directing at least a portion of the combined light to a multi-element detector so that different elements of the detector correspond to different illumination angles of a region of the test surface illuminated by the test light.

In some embodiments, the common source is a broadband spatially coherent source. The common source may be a broadband spatially coherent source. For example, in some embodiments the broadband source is a source spanning more than 50 nm at full width half maximum, more than 100 nm at full width half maximum, more than 500 nm at full width half maximum, or more than 1000 nm at full width half maximum.

In some embodiments, the directing spatially coherent test light to the test surface includes using an optical system to direct the test light to illuminate a test spot on the surface, where the width of the test spot at the test surface is about equal to a diffraction spot of the optical system at the test surface.

Some embodiments include processing angularly resolved information measured by the detector to determine information about the test object.

Some embodiments include: adjusting the relative optical path length between the test and reference light when they form the interference pattern and analyzing an interference intensity signal measured at each of multiple locations across the detector and produced by adjusting the relative optical path length.

In some embodiments, the adjusting the relative optical path length includes varying the optical path length over a range larger than a coherence length for the common source.

Embodiments may include any of the features or characteristics found in the various embodiments described above.

As used herein, "light" and "optical" does not only refer to visible electromagnetic radiation; rather such terms include electromagnetic radiation in any of the ultraviolet, visible, near-infrared, and infrared spectral regions.

"Spatially coherent" light is to be understood to refer to light where the oscillation of the electromagnetic field is substantially correlated for two or more points spatially separated in a direction transverse to the direction of propagation of the light.

Unless otherwise defined, all technical and scientific terms used herein have the same meaning as commonly understood by one of ordinary skill in the art to which this invention belongs. In case of conflict with any document incorporated by reference, the present disclosure controls.

Other features, objects, and advantages of the invention will be apparent from the following detailed description.

BRIEF DESCRIPTION OF THE DRAWINGS

Like reference numerals in different drawings refer to common elements.

DETAILED DESCRIPTION

Conventional techniques used for thin film characterization (e.g., ellipsometry) rely on the fact that the complex reflectivity of an unknown optical interface depends both on its intrinsic characteristics (e.g., material properties and thicknesses of individual layers) and on three properties of the light that is used for measuring the reflectivity: wavelength, angle of incidence, and polarization state. In practice, ellipsometry instruments record reflectivity fluctuations resulting from varying these parameters over known ranges. Optimization procedures such as least-squares fits are then used to get estimates for the unknown parameters by minimizing the difference between measured reflectivity data and a reflectivity function derived from a model of the optical structure.

Embodiments disclosed herein provide an interferometry system and method for rapidly collecting a large number of reflectivity data points over a wide range for all three optical characteristics of the probe beam (i.e., wavelength, angle of incidence, and polarization state) for a selected region of a test surface. Furthermore, the same instrument can switch from this ellipsometry mode of operation to a profiling mode to provide laterally resolved information about the test surface. Moreover, information determined in the ellipsometry mode can be used to improve the accuracy of the information obtained in the profiling mode. For example, the ellipsometry mode can provide information about the material properties of the test object having the test surface to create more accurate topography maps of the various optical interfaces, the top surface (air interface), for example, being of particular interest.

Exemplary Apparatus

Figure 1:
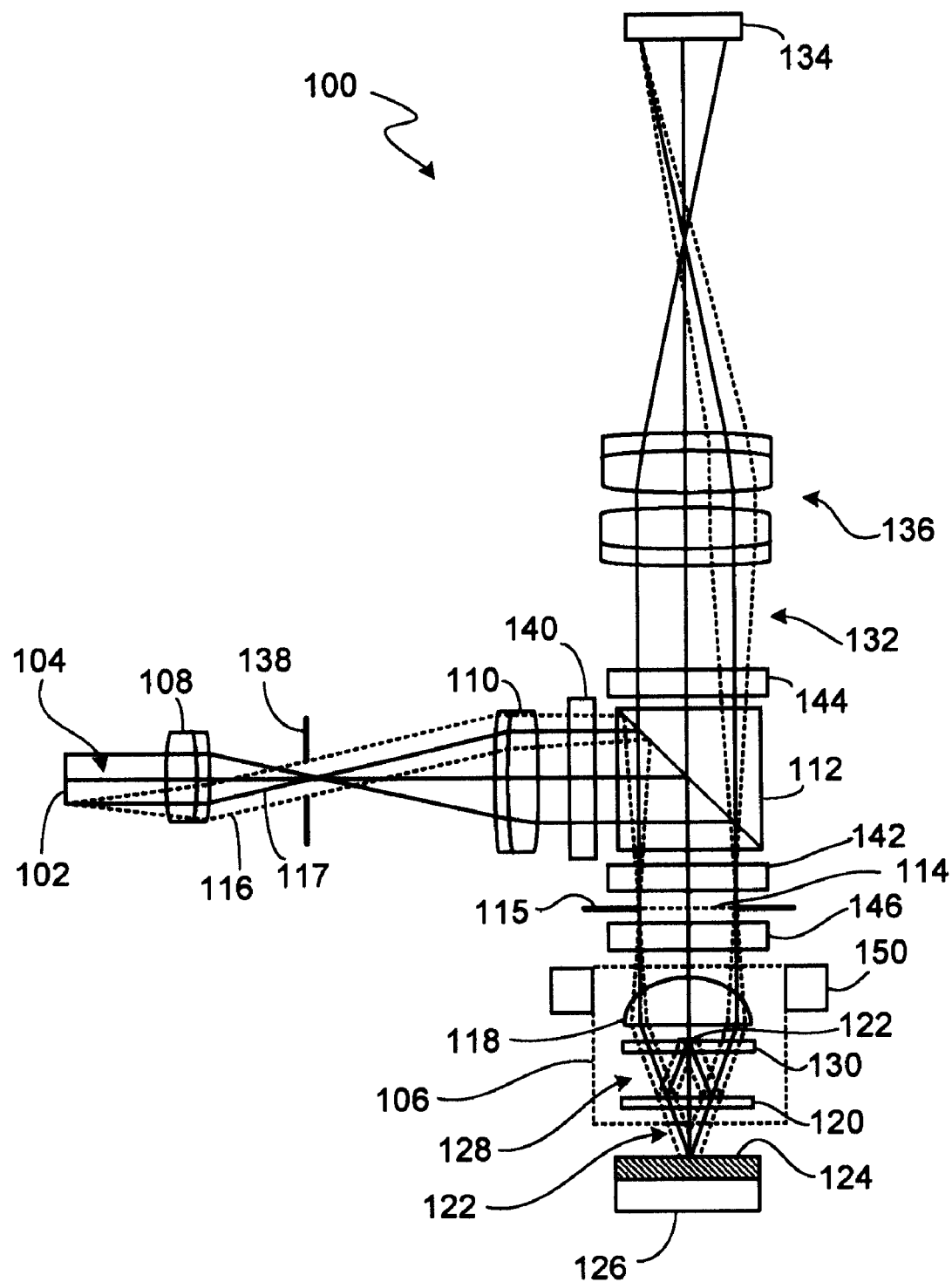
FIG. 1 is a schematic diagram of an interferometry system 100 configured to operate in an ellipsometry mode.

FIG. 1 is a schematic diagram of an interferometry system 100. A spatially extended source 102 directs input light 104 to an interference objective 106 via relay optics 108 and 110 and beam splitter 112. The relay optics 108 and 110 image input light 104 from spatially extended source 102 to an aperture stop 115 and corresponding pupil plane 114 of the interference objective 106 (as shown by the dotted marginal rays 116 and solid chief rays 117).

In the embodiment of the FIG. 1, interference objective 106 is of the Mirau-type, including an objective lens 118, beam splitter 120, and reference surface 122. Beam splitter 120 separates input light 104 into test light 122, which is directed to a test surface 124 of a test object 126, and reference light 128, which reflects from reference surface 122. Objective lens 118 focuses the test and reference light to the test and reference surfaces, respectively. The reference optic 130 supporting reference surface 122 is coated to be reflective only for the focused reference light, so that the majority of the input light passes through the reference optic before being split by beam splitter 120.

After reflecting from the test and reference surfaces, the test and reference light are recombined by beams splitter 120 to form combined light 132, which is transmitted by beam splitter 112 and relay lens 136 to form an optical interference pattern on an electronic detector 134 (for example, a multi-element CCD or CMOS detector). The intensity profile of the optical interference pattern across the detector is measured by different elements of the detector and stored in an electronic processor (not shown) for analysis. Unlike a conventional profiling interferometer in which the test surface is imaged onto the detector, in the present embodiment, relay lens 136 (e.g., a Bertrand lens) images different points on the pupil plane 114 to corresponding points on detector 134 (again as illustrating by dotted marginal rays 116 and solid chief rays 117).

Because each source point illuminating pupil plane 114 creates a plane wave front for test light 122 illuminating test surface 124, the radial location of the source point in pupil plane 114 defines the angle of incidence of this illumination bundle with respect to the object normal. Thus, all source points located at a given distance from the optical axis correspond to a fixed angle of incidence, by which objective lens 118 focuses test light 122 to test surface 124. A field stop 138 positioned between relay optics 108 and 110 defines the area of test surface 124 illuminated by test light 122. After reflection from the test and reference surfaces, combined light 132 forms a secondary image of the source at pupil plane 114 of the objective lens. Because the combined light on the pupil plane is then re-imaged by relay lens 136 onto detector 134, the different elements of the detector 134 correspond to the different illumination angles of test light 122 on test surface 124.

Polarization elements 140, 142, 144, and 146 define the polarization state of the test and reference light being directed to the respective test and reference surfaces, and that of the combined light being directed to the detector. Depending on the embodiment, each polarization element can be a polarizer (e.g., a linear polarizer), a retardation plate (e.g., a half or quarter wave plate), or a similar optic that affects the polarization state of an incident beam. Furthermore, in some embodiments one or more of the polarization elements can be absent. Moreover, depending on the embodiment, beam splitter 112 can be polarizing beam splitter or a non-polarizing beam splitter. Details of various embodiments for these polarization elements are described further below. In general, because of the presence of polarization elements 140, 142 and/or 146, the state of polarization of test light 122 at test surface 124 can be function of the azimuthal position of the light in pupil plane 114.

In the presently described embodiment, source 102 provides illumination over a broad band of wavelengths (e.g., an emission spectrum having a full-width, half-maximum of more than 50 nm, or preferably, even more than 100 nm). For example, source 102 can be a white light emitting diode (LED), a filament of a halogen bulb, an arc lamp such as a Xenon arc lamp or a so-called supercontinuum source that uses non-linear effects in optical materials to generate very broad source spectra (>200 nm). The broad band of wavelengths corresponds to a limited coherence length. As in conventional scanning interferometer, a translation stage 150 adjusts the relative optic path length between the test and reference light to produce an optical interference signal at each of the detector elements. For example, in the embodiment of the FIG. 1, translation stage 150 is a piezoelectric transducer coupled to interference objective 106 to adjust the distance between the test surface and the interference objective, and thereby vary the relative optical path length between the test and reference light at the detector.

Figure 2:
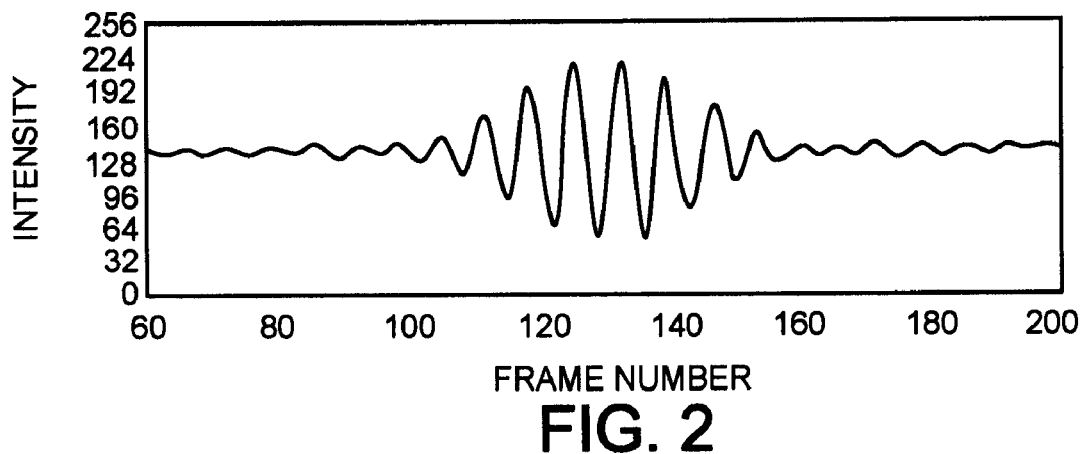
FIG. 2 is a graph showing an example of an interferometry signal measured a detector element when the optical path length difference ("OPD") between the test and reference light in interferometry system 100 is varied, where the OPD is expressed by frame number.

FIG. 2 shows an exemplary interference signal measured by one of the detector elements as the translation stage varies the relative optical path length between the test and reference light. The interference signal is modulated by a contrast envelope corresponding to the coherence length of the source. The reference surface is positioned in the interferometer so that a zero optical path length difference between the test and reference light corresponds to a position of the test surface that is in focus with respect to objective lens 118. Thus, maximum contrast is generally observed when the test surface is in this in-focus position relative to the interference objective. A measurement is performed by scanning the translation stage over a range larger than the coherence length so that the contrast envelope is captured in a sequence of intensity patterns measured at the detector.

The interference signal measured at each detector element is analyzed by the electronic processor, which electronically coupled to both detector 134 and translation stage 150. In the presently described embodiment, the electronic processor transforms the interference signal into the frequency domain, for example, by using a Fourier transform, to extract the phase and amplitude information for the different wavelength components of the light source. Preferably, the source spectrum is broad so that many independent spectral components can be calculated with this procedure. As will be described in greater detail below, the amplitude and phase data relate directly to the complex reflectivity of the test surface, which can be analyzed to determine information about the test object. Generally, the electronic processor uses information from a separate calibration to correct the measurement for the reflectivity of the reference mirror and other optical characteristics of the interferometer. Because of the arrangement of interferometry system 100, each detector element of electronic detector 134 provides reflectivity measurements at a multiplicity of wavelengths produced by source 102, for a specific angle of incidence and polarization state (according to the orientations of polarization elements 140, 142, 144 and/or 146). The collection of detector elements thus covers a range of angles of incidence, polarization states and wavelengths, which maximizes the ability of the instrument to properly characterize unknown optical structures.

A number of calibration procedures can be used to derive the complex reflectivity of the test surface from the measured interference signals. For example, a calibration measurement can be made with a mirror made of known bulk material (opaque or transparent) as the test object, and a spectral filter can be used to isolate a selected wavelength from the source. The interference signals measured on the detector can then be processed to determine the angle of incidence corresponding to each detector element and the speed of the scanning stage used for data acquisition. The latter information is useful to properly match the interference signal spectral components to their respective wavelengths. Additional measurements using objects of known optical properties can also be used to derive the properties of the interferometer and imaging system on a pixel-by-pixel basis. For example, a calibration may include the steps of calculating the transmission of the system for each wavelength and at each detector position. Similarly, polarization effects such as phase offsets introduced between orthogonal states of polarization can also be measured for each detector element and for each wavelength if required. Specific details for certain embodiments of the calibration are described further below.

Figure 3:
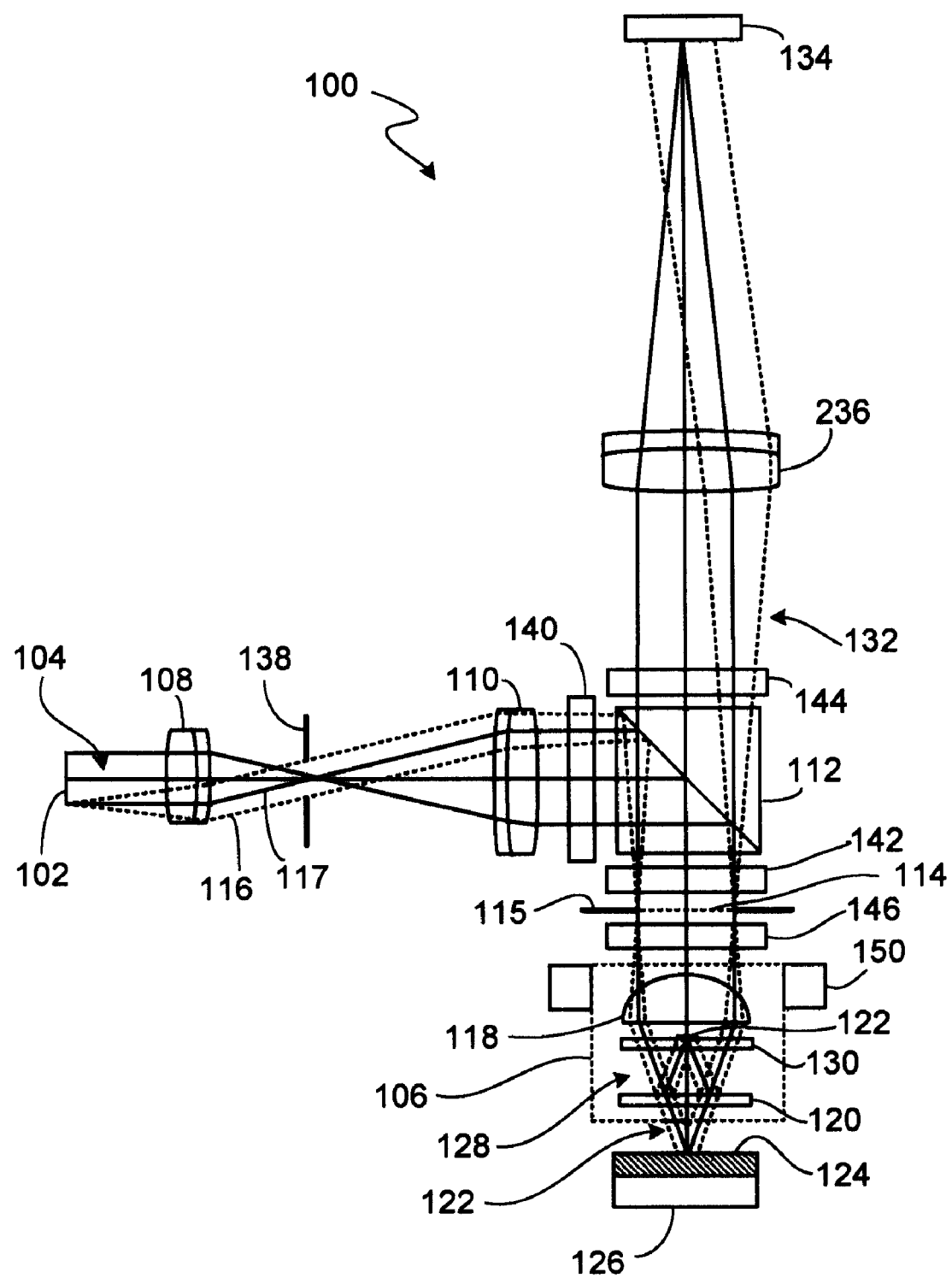
FIG. 3 is a schematic diagram of interferometry system 100 reconfigured to operate in a profiling mode.

To switch interferometry system 100 from an ellipsometry mode for a determining the complex reflectivity of the test surface, to a profiling mode for determining, for example, the topography of the test surface, it is sufficient to change the properties of the imaging system so that the image of the part comes in focus on the detector instead of the image of the source. As shown in FIG. 3, this can be accomplished, for example, by replacing the relay lens 136 by another lens 236 and keeping the detector position fixed. In this case, the input light from source 102 continues to be imaged to pupil plane 114, however, the points on 124 are imaged to corresponding points on detector 134 (as indicated by marginal rays 216 and chief rays 217 from source 102).

Measurement Model

To demonstrate the analysis of the interference signals obtained by interferometry system 100, we consider an embodiment in which polarization elements 140 and 144 are linear polarizers, polarization elements 142 and 146 are absent, and beam splitter 112 is a non-polarizing beam splitter. The effect of the linear polarizer 140 is to create an identical linear polarization state at every point in pupil plane 114. As a result, the polarization of the light incident on test surface 124 is linear, but its orientation with respect to the plane of incidence is a function of the azimuthal location of the source point at the pupil plane. For example, the source points that belong to a pupil diameter that is parallel to the direction of the linear polarization in the pupil plane will generate illumination light that is linearly polarized within the plane of incidence at the test surface (this is called the P polarization state). Similarly, the source points that belong to a diameter that is perpendicular to the direction of the linear polarization in the pupil plane will generate illumination light that is linearly polarized perpendicularly to the plane of incidence (this is called the S polarization state). Source points that do not belong to these two diameters will create illumination light on the test surface that has a mix of S and P polarization states. This is relevant because the reflectivity coefficients for the test surface are different for S and P polarized light.

The two linear polarizers can have a number of relative orientations that will dictate the content of the interference signal detected by the detector. For example, if the polarizers are parallel then the measured interference signal will depend solely on S-polarized test light being incident on the test surface for one diameter of the pupil plane and depend solely on P-polarized test light being incident on the test surface for an orthogonal diameter of the pupil plane (and similarly, for the reference light incident on the reference surface). This is attractive because the difference between the magnitude and phase of S and P reflectivities is the basis for ellipsometry. If desired, therefore, simplified processing of the data can be restricted to these two diameters. On the other hand, using the data over the entire pupil plane requires taking into account the mix of the two polarization states, but provides more data points and thus increases the resolution of the measurement.

The following analysis applies to the arrangement with the two linear polarizers aligned parallel to one another. In this case, the amount of test light that is transmitted through the second linear polarizer (polarization element 144) to detector 134 can be expressed as:

$$E_{out} = \frac{1}{2}(\cos(\theta)^2 rp \cdot tp - \sin(\theta)^2 rs \cdot ts)E_{in} \quad (1)$$

where θ is the azimuth angle measured with respect to the direction of the polarizers, rp and rs are the complex reflection coefficients of the object surface for P and S polarization states (known as the "Fresnel reflection coefficients"), tp and ts are the transmission coefficients for P and S polarization states for the round trip through the interference objective 106 and the main beam splitter 112 and $E_{out}$ is the complex amplitude of the electric field. This model assumes that the optics are free from birefringence and that reflection off the object surface is also free from mechanisms that would mix the S and P polarizations states. For example, a uniaxial material with its axis along the local surface normal can be characterized in this context, however, a material having in-plane birefringence requires a different model.

In practice, the same model applies for the reference light that propagates along the reference leg of the interferometer, however, the reflection and transmission coefficients are a priori different:

$$E_{out}^r = \frac{1}{2}(\cos(\theta)^2 rp^r \cdot tp^r - \sin(\theta)^2 rs^r \cdot ts^r)E_{in} \quad (2)$$

The interference pattern that is measured at the detector for a given source wavelength λ and a given source point at the pupil plane consists of a modulating term that is proportional to the produce $E_{out} E_{out}^r$:

Intensity$(k,\alpha,z)=|E_{out}|^2+|E_{out}^r|^2+2|E_{out}||E_{out}^r|\cos(2k$
$\cos(\alpha)z+\phi(k,\alpha))$ (3)

where k=2π/λ, λ is the wavelength of the light, z is the vertical location of the test surface during a mechanical scan relative to a zero optical path length difference between the test and reference light, α is the angle of incidence of the light at the test surface (which depends on the source point location at the pupil) and φ is a phase difference between the test and reference electric fields. In practice, the signal measured at a given detector location is the sum of all such signals generated by the various wavelengths present in the source spectrum. As a result, a Fourier transformation of the signal allows separating these contributions into complex spectral components corresponding to very narrow wavelength ranges. Note that in order to assign a calculated spectral component to a specific source wavelength one should take into account the correction factor cos (α), which shifts the location of these spectral components. This correction factor involves knowing the angle of incidence of light at each pixel of the detector. A calibration of the optical system can be used for this task and is discussed further below.

Figure 4:
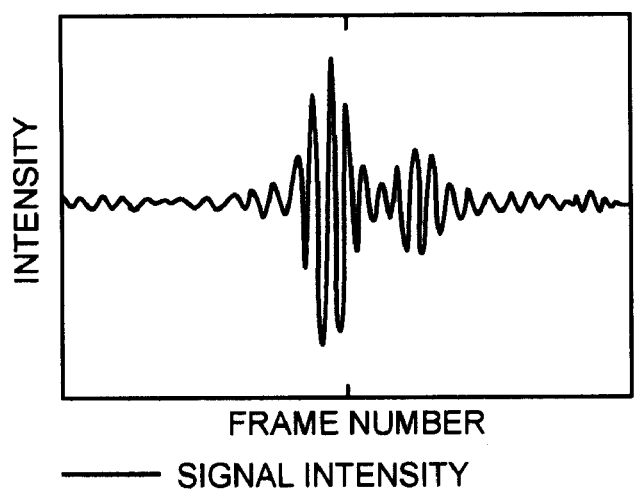
FIG. 4 shows plots of a data collected by a detector element for a test object having 1-micron thick silicon dioxide film on a silicon substrate. The left plot shows interferometry signal measured by the detector element as a function of frame number during the OPD scan. The right plot shows the Fourier transform of the interferometry signal with respect to wavenumber, with spectral magnitude being shown by solid trace and spectral phase being shown by the dotted trace.
Figure 4:
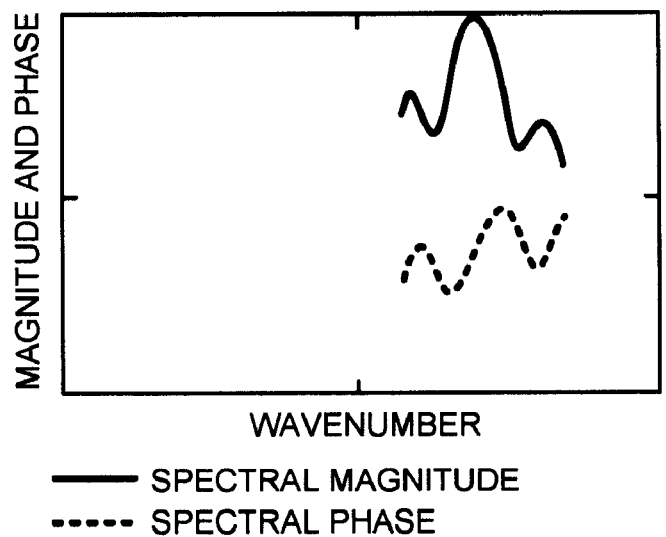

FIG. 4 (left side plot) shows a representative interference signal measured by a given detector element of detector 134 (corresponding to a given location in the pupil plane) when measuring a 1003-nm thick silicon dioxide film on silicon. FIG. 4 (right side plot) shows the result of Fourier transforming the interference signal to yield the spectral magnitude and phase as function of wavelength (or the corresponding wavenumber k). The variation in the spectral magnitude and phase is a result of the variation of the Fresnel reflection coefficient as a function of the wavelength (or wavenumber).

In certain embodiments, the frequency transform processing is applied to a region of interest within the image of the pupil plane on the detector. For example, the region of interest can be an annulus, which defines a given range of angles of incidence at the test surface. The azimuthal location of a pixel (i.e., one of the detector elements) within this annulus defines the mix of S and P polarization that illuminates the test surface and the radial distance of the pixel to the optical axis defines the angle of incidence. Furthermore, it can be useful to extract (possibly using interpolation) the spectral components as described above over multiple circles within the region of interest. These components calculated over one such circle can be written in the form:

$$Z_{\alpha\lambda\theta} = L_\lambda I_{\alpha\lambda\theta} \exp(i\varphi_{\alpha\lambda h})(\cos(\theta)^2 \rho_{\alpha\lambda} - \sin(\theta)^2 \tau_{\alpha\lambda}) \quad (4)$$

$$\text{with } \rho_{\alpha\lambda} = \frac{rp_{\alpha\lambda}}{rs_{\alpha\lambda}} \text{ and } \tau_{\alpha\lambda} = \frac{ts_{\alpha\lambda}}{tp_{\alpha\lambda}}$$

where the subscripts denote a functional dependence, $\alpha$ is the angle of incidence corresponding to the radius of the circle at the pupil plane, $\lambda$ is the wavelength of light, $\theta$ is the azimuthal angle measured with respect to the linear polarizers, h is height offset of the object surface, L is a real scaling factor related to the source intensity or signal strength and I is a complex function that represents the variations of the light intensity across the source as well as phase and amplitude variations occurring in the optics.

The electronic processor can use the above formula as the key model for the measurement process. For example, the processor can Fourier transform the interference signals recorded by the detector to yield the component Z for different wavelengths and angles of incidence and by inversion extract the complex ratio rp/rs that relates to the test surface being characterized (e.g., based on Eq. 4). This ratio is called the ellipsometric ratio and can also be expressed as:

$$\rho_{\alpha\lambda} = \frac{rp_{\alpha\lambda}}{rs_{\alpha\lambda}} = \tan(\Psi_{\alpha\lambda})\exp(i\Delta_{\alpha\lambda}) \quad (5)$$

where $\Psi$ and $\Delta$ are the two well-known ellipsometric parameters. Standard ellipsometry algorithms can then be used to calculate some optical properties of the test object, for example, the thickness and refractive index of transparent films.

For example, for the case of a homogeneous test surface devoid of films, the electronic processor can readily calculate the complex refractive index of the material according to the expression:

$$n(\lambda) = n_0 \tan(\alpha) \sqrt{1 - \frac{4\rho_{\alpha\lambda}}{(1+\rho_{\alpha\lambda})^2}\sin(\alpha)^2} \quad (6)$$

where $n_0$ is the refractive index of the ambient medium, usually air. The technique provides in this case the complex refractive index over the entire source spectrum. Data calculated over multiple angles of incidence can be averaged to improve the measurement resolution.

In another example, for the case of a transparent monolayer having an unknown thickness t and known refractive indices $n_0$, $n_1$, $n_2$ of the ambient, film and substrate materials, the electronic processor can determine the unknown thickness t according to the following equations:

$$\alpha_0 = \alpha, \; \alpha_1 = \frac{n_0(\lambda)}{n_1(\lambda)}\sin(\alpha_0), \; \alpha_2 = \frac{n_1(\lambda)}{n_2(\lambda)}\sin(\alpha_1) \quad (7)$$

$$r_{01p} = \frac{\tan(\alpha_0 - \alpha_1)}{\tan(\alpha_0 + \alpha_1)}, \; r_{12p} = \frac{\tan(\alpha_1 - \alpha_2)}{\tan(\alpha_1 + \alpha_2)}$$

$$r_{01s} = \frac{\sin(\alpha_0 - \alpha_1)}{\sin(\alpha_0 + \alpha_1)}, \; r_{12s} = \frac{\sin(\alpha_1 - \alpha_2)}{\sin(\alpha_1 + \alpha_2)}$$

$$A = r_{01p}, \; B = r_{12p} + r_{01p}r_{01s}r_{02s}, \; C = r_{12p}r_{01s}r_{12s}$$

$$D = r_{01s}, \; E = r_{12s} + r_{01p}r_{01s}r_{12p}, \; F = r_{01p}r_{12p}r_{12s}$$

$$X = \frac{-(B-\rho_{\alpha\lambda}E) \pm \sqrt{(B-\rho_{\alpha\lambda}E)^2 - 4(C-\rho_{\alpha\lambda}F)(A-\rho_{\alpha\lambda}D)}}{2(C-\rho_{\alpha\lambda}F)}$$

$$t = \frac{i\lambda}{4\pi n_1(\lambda)\cos(\alpha_1)}\log(X)$$

where log is the complex natural logarithm function, $i=\sqrt{-1}$ and the sign in the calculation of X is chosen according to the resulting value of $\tau$, which must be real positive. The processing of the data obtained by interferometry system 100 provides multiple estimates of t, because the measurement is performed for multiple values of $\alpha$ and $\lambda$. These multiple estimates can be used to solve for a possible ambiguity in the film thickness associated with the term X in Eq. 7 and to improve the measurement resolution. In other embodiments, the electronic processor can derive one or more of the refractive indices of the test object from the measurement data based on a similar set of equations.

For more general cases, the electronic processor can use, for example, the "scattering matrix" approach to calculate the reflection coefficients of an test surface as a function of its unknown parameters (refractive indices, film thicknesses, layer roughness, refractive index gradients, etc). The reflection coefficient functions are applied to calculate the ellipsometric parameters $\Psi^{model}$ and $\Delta^{model}$ for guess values of the unknown parameters. An iterative algorithm is then used to vary these parameters in order to minimize the sum of the squared differences between the measured ellipsometric coefficients and corresponding model coefficients:

$$\chi^2 = \Sigma(\Psi_{\alpha\lambda} - \Psi_{\alpha\lambda}^{model})^2 + \Sigma(\Delta_{\alpha\lambda} - \Delta_{\alpha\lambda}^{model})^2 \quad (8)$$

Alternative merit functions can be defined that include for example weighting factors for the different wavelengths and angles of incidence. Such approaches are described, for example, in R. M. A. Azzam and N. M. Bashara, "Ellipsometry and Polarized Light," Elsevier Science B.V., ISBN 0 44 870164 (paperbook), 1987.

System Calibration

In certain embodiments, a first step of the system calibration includes calculating the angle of incidence of a beam bundle at the test surface based on the location of the source point in the pupil plane. In other words, we want to assign an angle of incidence $\alpha$ to each pixel in the detector corresponding to the image of the pupil plane. This can be accomplished, for example, by performing a measurement with a narrow-band filter so that the light detected by the detector is essentially monochromatic and has a known wavelength. In this case, Equation (3) shows that the frequency of the interference signal is proportional to the source wavelength and the angle of incidence through the relationship k cos $\alpha$. The signal frequency can be calculated by a Fourier transform of the signal and the angle of incidence can be derived from the knowledge of the scan rate of the translation stage and the source wavelength.

Furthermore, to the extent the scan rate of the translation stage is initially unknown, it can be determined by locating the pixel on the detector whose interference signal has the largest frequency. According to the frequency's dependence on the relationship k cos α, this pixel corresponds to normal incidence (i.e., α=0), and so the stage speed can be extracted directly from the measured frequency and knowledge of the source wavelength.

Note that a priori information on the way the microscope objective maps angles in object space onto pupil positions can also be used to improve the quality of this calibration. For example, a typical objective is corrected for coma (a geometric aberration), which implies that the ray mapping at the pupil should nominally obey the so-called "Abbé sine condition." This condition means that the radial distance of a source point from the optical axis at the pupil is directly proportional to the sine of the angle of incidence in object space. One can thus calculate the angle of incidence for each pixel and then fit a global function derived from the sine condition to provide an analytical function mapping pupil position to angle of incidence.

In certain embodiments, the procedure outlined above can be repeated for different nominal source wavelengths so that chromatic variations of the angular mapping are taken into account. A by-product of the fitting procedure is the pixel position of the optical axis at the pupil. That information is also recorded as a function of wavelength and can be used later on to apply corrections to angle of incidence calculations.

For certain embodiments, the second stage of the calibration involves calculating the value of the various system parameters that relate the observable Z expressed in in Eq. 4) to the ellipsometric ratio.

For example, this can accomplished by measuring two samples that have known optical properties, for example calibration wafers typically used with ellipsometers. For each angle of incidence and wavelength of interest the electronic processor determines the spectral components Z as a function of azimuth angle θ as in Eq. (4) for both samples. The ratio of these components is then calculated, yielding the complex ratio z as a function of θ.

$$z_{\alpha\lambda\theta} = \frac{Z^a_{\alpha\lambda\theta}}{Z^b_{\alpha\lambda\theta}} = \frac{L^a_\lambda}{L^b_\lambda}\exp(i\varphi_{\alpha\lambda ha} - i\varphi_{\alpha\lambda hb})\frac{\cos(\theta)^2 \rho^a_{\alpha\lambda} - \sin(\theta)^2 \tau_{\alpha\lambda}}{\cos(\theta)^2 \rho^b_{\alpha\lambda} - \sin(\theta)^2 \tau_{\alpha\lambda}} \quad (9)$$

or $$z_{\alpha\lambda\theta} = zs_{\alpha\lambda}\frac{\cos(\theta)^2 \rho^a_{\alpha\lambda} - \sin(\theta)^2 \tau_{\alpha\lambda}}{\cos(\theta)^2 \rho^b_{\alpha\lambda} - \sin(\theta)^2 \tau_{\alpha\lambda}}$$

where $zs_{\alpha\lambda}$ and $t_{\alpha\lambda}$ are unknown complex numbers and the a or b subscripts identify one or the other calibration sample. $\rho^a_{\alpha\lambda}$ and $\rho^b_{\alpha\lambda}$ are calculated using the ratio of the reflection coefficients for the two materials. These coefficients are themselves calculated using the known material properties and known film thicknesses (if present) of the calibration samples. The electronic processor can then use a solver, for example a least-squares solver based on the Levenberg-Marquardt algorithm, to find the value of the two unknown parameters that minimize the difference between the quantities calculated on both sides of Equation (9). The process is repeated for other angles of incidence and wavelengths.

In a further step, if desired, the maps $zs_{\alpha\lambda}$ and $t_{\alpha\lambda}$ are filtered and/or fitted to analytical functions. It is then possible to reprocess the spectral components obtained for each sample and derive another calibration parameter, the function J:

$$J_{\alpha\lambda\theta} = \frac{Z^a_{\alpha\lambda\theta}}{\cos(\theta)^2 \rho^a_{\alpha\lambda} - \sin(\theta)^2 \tau_{\alpha\lambda}} = L^a_\lambda I_{\alpha\lambda\theta} \exp(i\varphi_{\alpha\lambda ha}) \quad (10)$$

or $$J_{\alpha\lambda\theta} = \frac{Z^b_{\alpha\lambda\theta}}{\cos(\theta)^2 \rho^b_{\alpha\lambda} - \sin(\theta)^2 \tau_{\alpha\lambda}} zs_{\alpha\lambda} = L^a_\lambda I_{\alpha\lambda\theta} \exp(i\varphi_{\alpha\lambda ha})$$

In practice, the two expressions for J shown in Equation (10) can be averaged. The calculated values of J as a function of angle of incidence, wavelength and azimuth angle are then stored by the electronic processor in a calibration file along with the definition of the function $\tau_{\alpha\lambda}$.

Note that the procedure outlined above could be extended to more than two samples in order to benefit from redundancy in the calculation.

In certain embodiments, another step of the calculation involves establishing the exact angular orientation of the polarizers with respect to the coordinate system of the pupil as seen by the detector. This can be done, for example, by observing that Equation (9) is periodic in θ with a period π. It follows that the phase of the even components of the Fourier transform of the ratio z is a direct measurement of the angular offset of the polarizer. Accordingly, this calculation can be performed before determining $zs_{\alpha\lambda}$ and $\tau_{\alpha\lambda}$.

Characterization of an Unknown Test Object

In certain embodiments, by using the stored calibration information, the electronic processor can characterize an unknown test object as follows. The interference data recorded for an unknown object surface are processed as for the calibration and yield rings of data according to Equation (4), where the superscript c denotes the unknown test object:

$$Z^c_{\alpha\lambda\theta} = L^c_\lambda I_{\alpha\lambda\theta}\exp(i\phi_{\alpha\lambda hc})(\cos(\theta)^2 \rho^c_{\alpha\lambda} - \sin(\theta)^2 \tau_{\alpha\lambda}) \quad (11)$$

Each ring is processed using the calibration information. First, the function J is retrieved for the specific angle of incidence and wavelength and a new complex ratio is calculated:

$$z_{\alpha\lambda\theta} = \frac{Z^c_{\alpha\lambda\theta}}{J_{\alpha\lambda\theta}} = \frac{L^c_\lambda}{L^a_\lambda}\exp(i\varphi_{\alpha\lambda hc} - i\varphi_{\alpha\lambda ha})(\cos(\theta)^2 \rho^c_{\alpha\lambda} - \sin(\theta)^2 \tau_{\alpha\lambda}) \quad (12)$$

or $$z_{\alpha\lambda\theta} = \frac{Z^c_{\alpha\lambda\theta}}{J_{\alpha\lambda\theta}} = \eta_{\alpha\lambda}(\cos(\theta)^2 \rho^c_{\alpha\lambda} - \sin(\theta)^2 \tau_{\alpha\lambda})$$

where $\eta_{\alpha\lambda}$ and $\rho^c_{\alpha\lambda}$ are unknown complex parameters independent of the azimuth angle θ. A numerical solver is applied again to find the value of these parameters that provide the best match between the measured ratio z and the model on the right hand side of Equation (12). An important result of the calculation is the parameter $\rho^c_{\alpha\lambda}$, which is the ellipsometric ratio for the unknown object surface.

As described above with reference, for example, to Eqs. 6-8, the electronic processor can process the ellipsometric ratio according to a model of the test object to extract information about the test object, such as the refractive index and/or thickness of one or more layers.

Figure 5:
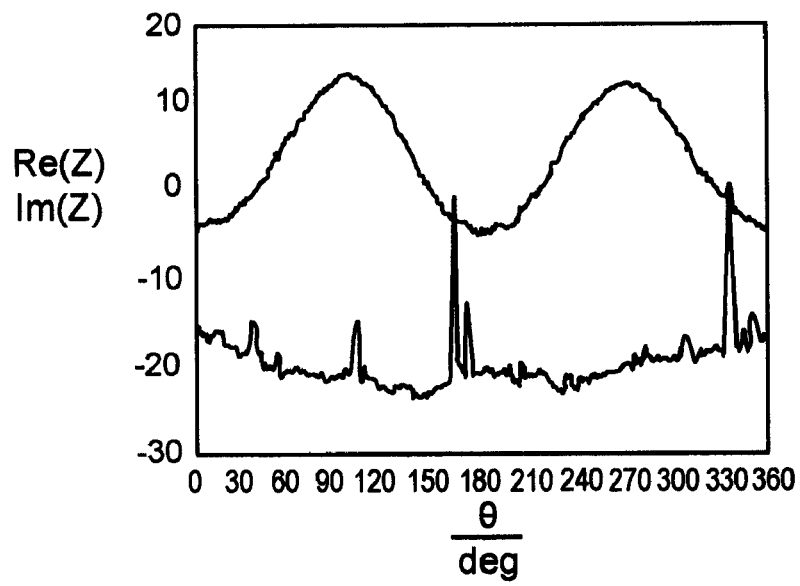
FIG. 5 shows plots of experimentally derived, complex reflectivity coefficients for a selected angle of incidence (43 degrees) and a selected wavelength (576 nm) as a function of azimuth angle for a 675-nm thick silicon dioxide monolayer film on a silicon substrate. The left plot shows the spectral component (top curve being the real component and the bottom curve being the imaginary component) and the right plot shows the corresponding values for (top curve being the real component and the bottom curve being the imaginary component), which scales Z with respect to a system calibration.
Figure 5:
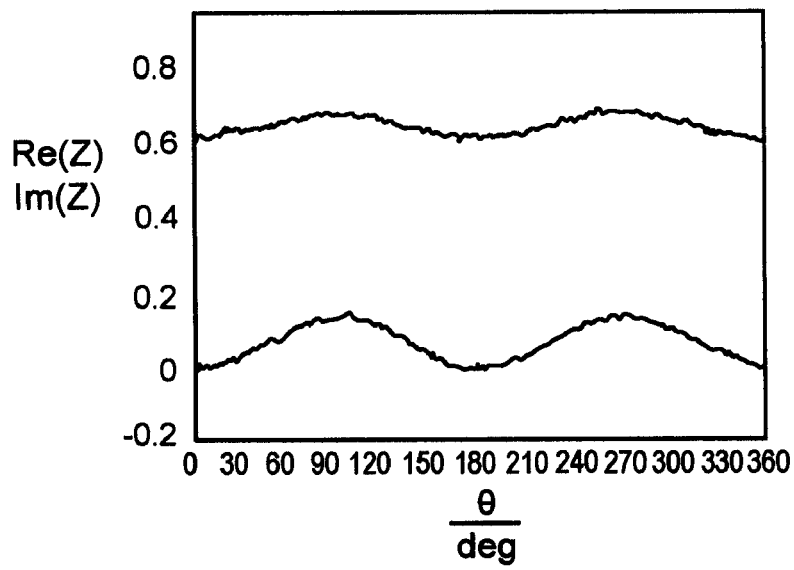

The graphs in FIG. 5 show experimental data derived using the above analysis for a 675-nm thick $SiO_2$ monolayer on a silicon substrate. The graphs show the real and imaginary parts of $Z^c_{\alpha\lambda\theta}$ (left side plot) and $z_{\alpha\lambda\theta}$ (right side plot) measured experimentally for $\alpha=43°$ and $\lambda=576$ nm. As shown, the derived ration $z_{\alpha\lambda\theta}$ exhibits the $\pi$-periodicity expected from the model in Equation (12).

Note that in order to create the ring of data defined in Equation (11), the location of the optical axis at the detector should be known. This location may have changed since the calibration. For example, because the instrument may have been switched from the surface characterization mode to the topography mode, one cannot assume that the projection of the center of the pupil at the detector remains constant. Hence, in certain embodiments, a preliminary step of the process can involve calculating the frequency spectrum at each detector element, deriving a nominal mean frequency for each pixel (e.g., the mean frequency can be calculated as the centroid of the measured spectrum), and analyzing the map of mean frequency to find the location of the pupil center. As mentioned in the calibration section above, the mean frequency for a given source spectrum is expected to scale with the cosine of the angle of incidence in object space. Hence, the pupil location where the mean frequency is maximum corresponds to the optical axis. In some embodiments, this location can be calculated by fitting an even function—such as a parabola—to the map of mean frequencies and defining the apex of the parabola as the location of the optical axis. Alternatively, a preliminary measurement can be performed with a narrowband filter inserted in the system, as in the system calibration.

For simplicity and ease of expression, the procedures outlined in the above sections are based on certain assumptions about the nature of the test surface and the optical system. However, more advanced models can be used for more complicated cases to extract information about the test object from the interference signals measured by system 100. For example, a different model can be used when the test structure may exhibit birefringence, while the calibration procedure based on non-birefringent calibration samples remains the same.

Additional Configurations of the Polarization Elements

The analytical sections above were based on an embodiment in which polarization elements 140 and 144 are linear polarizers oriented parallel to one another, polarization elements 142 and 146 are absent, and beam splitter 112 is non-polarizing. In another embodiment, an analytically equivalent configuration that guarantees the parallelism of the linear polarizers involves removing polarization elements 140 and 144, and having polarization element 142 being a linear polarizer, because it is positioned in the path of both the input light being directed to the interference objective and the combined light being directed to the detector. In another embodiment, polarization elements 140 and 144 can be linear polarizers that oriented orthogonal to one another, in which case the amount of light coming back from the object is a periodic function of the azimuthal position multiplied by an azimuth-independent weighted sum of the S and P reflectivity. Such information can also be processed to determine information about the test object.

In yet another embodiment, polarizing elements 140, 144 and 146 are absent, whereas the beam splitter 112 is of the polarizing type and polarization element 142 is a quarter wave plate. Proper alignment of the quarter wave plate with its fast and slow axes at 45° from the polarization axis defined by beam splitter 112 results in a circular polarization state at every point of the pupil. The contribution of S and P polarizations in the detected interference signal is then to first-order independent of the azimuthal position of the source points. It is thus possible to combine the information collected over groups of detector elements that reside at fixed distances from the optical axis to improve the signal to noise ratio of the overall measurement. Note that depending on the nature of the quarter wave plate more advanced processing may be required to account for example for the variation of retardance with wavelength, which introduces a small azimuthal dependence on the polarization state of the source points at the pupil. This can be modeled mathematically using, for example, Jones matrices and vectors, as is known in the art.

In yet another embodiment, polarization element 140 is absent, bean splitter 112 is of the polarizing type, polarization element 142 is a quarter wave plate, polarization element 144 is absent, and polarization element 146 is a linear polarizer attached to interference objective 106. Because of the linear polarizer, this embodiment is analytically equivalent to the first embodiment with parallel linear polarizers. However, the addition of a polarizing beam splitter and quarterwave plate improves the light efficiency of the system when a different microscope objective (without polarizer attached) is mounted to the system, for use, for example, in the profiling mode of operation. As described in greater detail below, switching back and forth between different microscope objectives can be accomplished with an objective turret, which can be motorized under the control of the electronic processor for a production line instrument.

Reflectometry Mode

In yet another embodiment, polarization elements 140, 142, 144 and 146 are all absent and the beam splitter is of the non polarizing type. For a typical broadband source such as the filament in a halogen bulb or the emissive material of a white-light LED, the illumination input light is unpolarized, which means that for every source point at the pupil the polarization state can be described as an equal mix of S and P polarization components. In this case the measured signal is expected to be again independent from the azimuthal source position to the first order. In this case the system is capable of measuring the amount of light reflected by the object for different angles of incidence, as in a reflectometer. However, contrary to a conventional reflectometer that captures light one wavelength at a time, interferometry system 100 can capture all source wavelengths in the course of a single measurement. These spectral components are separated using the analysis of the signal in the frequency domain described above. While this reflectometry mode of operation does not provide as much information about the test surface reflectivity as the ellipsometry modes described above, the reflectometry information is still sensitive to variations in the properties of the test object. For example, the reflectometry data can be compared to models of the test object to determine the material composition at a given location in a heterogeneous sample, refractive indices, thicknesses, and/or the presence or absence of defects.

Selective Signal Analysis For Thin Film Samples

When the test object includes one or more films, the multiple interfaces produce multiple reflections that contribute the interference signal measured at each detector element. For the case of a broadband light source, the interference signal measured at various locations at in pupil plane have a limited coherence length, as shown by the signal envelope in FIG. 2 and FIG. 4 (left side). When the film is sufficiently thick that the round-trip optical thickness is larger than the coherence length, the measured signal consists of multiple separable signals, each signal corresponding to an interface between two materials.

Figure 6:
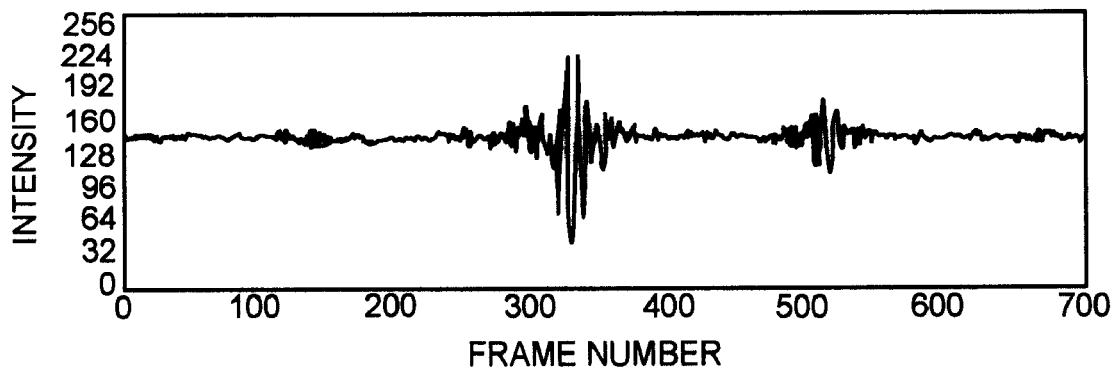
FIG. 6 shows a plot of the interferometry signal for a 5-micron thick film of silicon dioxide on silicon to demonstrate how portion of the signal can be selected to isolate a selected interface in the structure.

An example of such a signal is shown in FIG. 6 for a 5-μm thick silicon dioxide ($SiO_2$) film on silicon (Si). In this case, the weaker signal to the right corresponds to the air/$SiO_2$ interface. The larger signal in the center corresponds to the $SiO_2$/Si interface. The weak signal on the left is due to a double pass reflection of light in the $SiO_2$ layer. In this case, it is possible to process each portion of the signal corresponding to a given interface independently to simplify or improve the robustness of the analysis.

For example, in certain embodiments, the electronic processor may process the portion of the signal corresponding to the air/top layer interface so that the analysis becomes equivalent to measuring an infinitely thick slab of the top layer material. In this case the refractive index of the material can be readily calculated using Equation (6) and there is no need to include in the modeling the effect of underlying layers and possibly complex structures such as those found on patterned semiconductor wafers.

Furthermore, in certain embodiments, after the electronic processor analyzes the portion of the signal corresponding to the top interface, the processing can be repeated for the entire signal (or other portions of the signal) by including the signal portions corresponding to the underlying interface. The model required to process the ellipsometry data is more complicated in this case, however, because the initial processing yields the refractive index of the top layer, the processing is simpler than it would have been in the absence of the initial processing. For example, the refractive index of a thick monolayer can be first calculated using Equation (6) when processing the rightmost signal. Assuming the substrate material is known, the processing of the entire interference signal (including the entire trace shown in FIG. 6, for example) yields new ellipsometric parameters that provide the film thickness using Equation (7). The benefit is the ability to separate the calculation of the refractive index and physical thickness.

For the case of a multilayer stack made of sufficiently thick layers, one can apply a bootstrap procedure that starts with the first signal yielding the refractive index of the first layer. The processing of the first and second signals simultaneously then yields the thickness of the first layer and the refractive index of the second layer. The processing of the first, second and third signals then yields the thickness of the second layer and the refractive index of the third layer, and so on. The benefit again is that one does not need to use an ellipsometric model that includes all interfaces at once with all materials and thicknesses being unknowns, as is common in conventional ellipsometers.

Even for small film thicknesses that cause the interference signal associated with each interface to partially overlap, it may still be possible to isolate a portion of the interference signal corresponding to a given interface and separately process that portion. See, for example, U.S. patent application Ser. No. 10/941,649 entitled "METHODS AND SYSTEMS FOR INTERFEROMETRIC ANALYSIS OF SURFACES AND RELATED APPLICATIONS" and published as U.S. Patent Publication No. US-2005-0078318-A1, the contents of which are incorporated herein, which describes such techniques in the context of a profiling mode.

Profiling Mode Analysis

As described above, interferometry system 100 can switch from an ellipsometry (or reflectometry) mode for a determining reflectivity information about the test surface, to a profiling mode for determining, for example, the topography of the test surface. As shown in FIG. 3, this can be accomplished, for example, by replacing the relay lens 136 by another lens 236 that images test surface to the detector (rather than image the pupil plane to the detector). This configuration corresponds to a conventional scanning interferometer for surface profiling. In what follows, a mathematical formalism for the surface profiling operation is described.

For a bulk material test object (i.e., no thin film structure), the interference phase φ to first order in the angular wavenumber $k=2\pi/\lambda$ with respect to a reference datum plane in the test leg can be expressed as:

$$\phi(k) = 2nk(h-\zeta) + (\gamma_{part} + \gamma_{sys}) + (\tau_{part} + \tau_{sys})(k - k_0) \quad (13)$$

where $k_0$ is the nominal wavenumber, ζ is the scan coordinate for the translation stage, $\gamma_{part}$ is the part surface phase change on reflection (PCOR), and $\gamma_{sys}$ is the system phase offset attributable to the interferometer system. The value $\gamma_{sys}$ includes PCOR contributions from the interferometer optics and any constant offsets resulting, e.g., from the starting position of the scan ζ. The linear dispersions coefficients $\tau_{part}$ and $\tau_{sys}$ correspond to the phase offsets $\gamma_{part}$ and $\gamma_{sys}$, respectively. The phase offsets $\gamma_{part}$, $\gamma_{sys}$ are evaluated at the nominal wavenumber $k_0$. The index of refraction n for air and is assumed to be independent of wavenumber. Those skilled in the art will appreciate that the teachings of the invention can be extended to denser transparent media than air by taking into account the wavenumber dependence of material index. All of the terms in Eq. 13 are potentially a function of field position x,y, although for the subsequent description, the variables n, ζ, $k_0$ are assumed to be constant over the field of view.

Because of the broad brand radiation from the light source, interference fringes are only produced when the optical path difference (OPD) between the reference and measurement legs are within the coherence length of the broadband radiation. Thus, scanning interferometric measurements can be considered a "coherence profiling" mode in that it uses the broadband nature of the interference effect, e.g., the localization of fringe contrast or equivalently, the measurement of the rate of change of interference phase with wavenumber. As a result, the interference signal I measured by each detector element can be expressed as:

$$I = 1 + V[h + (\tau_{sys} + \tau_{part})/2n - \zeta] \cos[2nk_0(h-\zeta) + \gamma_{part} + \gamma_{sys}] \quad (14)$$

where V is the fringe contrast envelope. The envelope V is proportional to the Fourier Transform of the spectral distribution of the light from the light source.

For a symmetric contrast envelope, the peak value of the fringe contrast envelope is given by the scan position for which dφ/dk=0. This is the stationary phase position, where the interference phase is the same independent of wave number, and all of the interference patterns add up constructively. More generally, it can be shown that the stationary phase condition dφ/dk=0 corresponds to the centroid of the fringe contrast envelope V. The phase gap G between the stationary phase position and the nearest zero phase point φ=0 position is given by $$G = (\gamma_{part} + \gamma_{sys}) - k_0(\tau_{sys} + \tau_{part}). \quad (15)$$

This is a constant phase offset, independent of wavenumber k, but dependent on the system and part parameters. The phase $\phi_0$ is the phase at the nominal wavenumber $k_0$ (with respect to a ζ=0 scan position), e.g., from Eq. (13) we have $$\phi_0 = 2nk_0 h + (\gamma_{part} + \gamma_{sys}). \quad (16)$$

From Eq. 14 it can be seen that the maximum or peak fringe contrast occurs at the scan position $\zeta = h + (\tau_{sys} + \tau_{part})/2n$. Thus, in one data processing embodiment, the electronic processor, when operating in the profiling mode, determines the fringe-contrast envelope V as a function of $\zeta$, e.g., by electronic or digital conversion, for every detector pixel. It then determines the scan position $\zeta_{max}$ for which the envelope V reaches a specific value, e.g., its maximum or peak value. The corresponding height h for each location on the test object is this scan position minus the dispersion offset:

$$h = \zeta_{max} - (\tau_{sys} - \tau_{part})/2n. \quad (17)$$

In another signal processing method, the coherence profiling intensity signal is Fourier transformed with respect to the scan position $\zeta$ into the frequency domain (i.e., with respect to frequency wave number k). The phase of the transformed data corresponds directly to the phase $\phi(k)$ in eq. 13. From this phase, the signal processor calculates the phase derivative $d\phi/dk$, and determines height h for each detector pixel according to:

$$h = \frac{1}{2n}\frac{d\phi}{dk} - (\tau_{sys} - \tau_{part})/2n \quad (18)$$

where the derivative $d\phi/dk$ is calculated for $\zeta=0$. Eq. 18 follows directly from Eq. 13.

From Eqs. 17 and 18, one sees that surface height measurements based on coherence profiling data can be more accurately calculated by accounting, e.g., by calibration, for PCOR dispersion for the interferometry system and the test part (e.g., $\tau_{part}$ and $\tau_{sys}$). To the extent the PCOR factors are constant across the field of view, not accounting for them will only introduce overall shift in the surface profile and the resulting surface topography is accurate. However, when the PCOR factors change because of, for example, variations in the surface material, they should be accounted for to provide a more accurate surface topography profile.

In addition to coherence profiling, surface height measurements can also be based on interferometric phase profiling data where the interferometric phase $\phi(k)$ is measured directly for one or more wavenumbers k. For example, phase shifting interferometry (PSI) techniques can be used for such measurements. From Eq. 13, it is clear that if direct interferometric phase measurements are used to determine height h, accounting for PCOR $\gamma_{part}$ and $\gamma_{sys}$ (and PCOR dispersion $\tau_{part}$ and $\tau_{sys}$ for wave numbers other than the nominal wave number $k_0$) improves the accuracy of the height measurement.

Generally, the sensitivities to particular noise sources for coherence profiling measurements differ from those for phase profiling measurements, thus a particular technique may be preferable for a particular application, or they may be used to complement one another. One drawback of many phase profiling measurements, however, is the measured phase $\phi(k)$ includes $2\pi$ fringe ambiguity. For relatively smooth surfaces, relative fringe ambiguity over the surface may be interpolated from the data of multiple detector pixels using standard fringe unwrapping procedures. More generally, however, it is preferable to have an independent measurement, such as coherence profiling data, to remove such fringe ambiguity. Thus, to obtain absolute surface profile measurements, the coherence profiling height measurement can be used alone, or it can be used to remove the absolute fringe ambiguity from the phase profiling measurement, which may be more accurate than the coherence measurement in some cases.

In one such embodiment, the height h determined from a coherence profiling measurement is used to calculate an absolute phase profiling height measurement h' based on phase profiling data for the phase $\phi_0 = \phi(k_0)$ according to:

$$h' = \frac{1}{2nk_0}\left\{(\phi_0 - \gamma_{part} - \gamma_{sys}) - 2\pi \text{Int}\left[\frac{(\phi_0 - \gamma_{part} - \gamma_{sys}) - (2k_0 nh)}{2\pi}\right]\right\} \quad (19)$$

where Int [ ] returns the nearest integer to its argument. Eq. 19 can be applied independently to every point x,y on the part surface. Again, as is apparent from Eq. 19, accounting for PCOR $\gamma_{part}$ and $\gamma_{sys}$ improves the accuracy of the absolute phase profiling measurement. Moreover, Eq. 19 implicitly depends on PCOR dispersion values $\tau_{part}$ and $\tau_{sys}$ through the coherence profiling determination of h.

For more complex samples, such as those with thin films, the profiling formalism is more complicated because reflections from underlying surfaces will also contributed the interference signal. Where the limited coherence length of input light is small enough relative to film thickness to separate the interferometry signal into portions corresponding to each interface, the electronic processor can isolate that portion of the interferometry signal corresponding to the interface of interest and process it using the general formalism described above to extract the surface topography for that interface. Furthermore, even for small film thicknesses that cause the interference signal associated with each interface to partially overlap, it may still be possible to isolate a portion of the interference signal corresponding to a given interface and separately process that portion. See, for example, U.S. patent application Ser. No. 10/941,649 entitled "METHODS AND SYSTEMS FOR INTERFEROMETRIC ANALYSIS OF SURFACES AND RELATED APPLICATIONS" and published as U.S. Patent Publication No. US-2005-0078318-A1, which was incorporated by reference above. In yet further embodiments, the electronic processor can use the model-based techniques disclosed in U.S. patent application Ser. No. 10/795,579 entitled "PROFILING COMPLEX SURFACE STRUCTURES USING SCANNING INTERFEROMETRY" and published as U.S. Patent Publication No. US-2004-0189999-A1, the contents of which is incorporated herein by reference, to determine profile information for complex surface structures.

Additional Embodiments for Profiling

Figure 7:
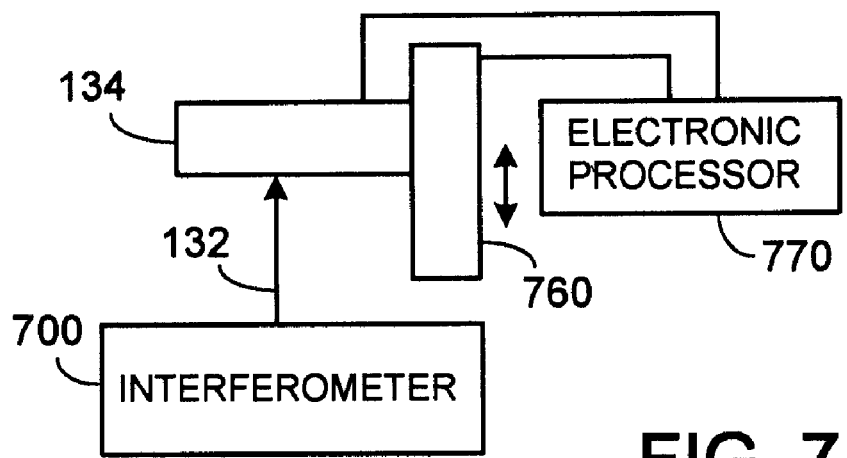
FIG. 7 is a schematic diagram of another embodiment for interferometry system 100.

Instead of switching out relay lens 136, in further embodiments, for example, the relay lens can be left alone and detector 134 can be translated to a position where the test surface is in focus. This is shown schematically in FIG. 7, which shows detector 134 coupled to a motorized translation stage 760 under the control of electronic processor 770 to adjust the detector position for receiving combined light 132 relative to the rest of the interferometry system 700. The translation stage allows the system to switch between a first position corresponding the ellipsometry mode, in which the pupil plane is imaged to the detector, and a second position corresponding to the profiling mode, in which the test surface is imaged to the detector.

Figure 8:
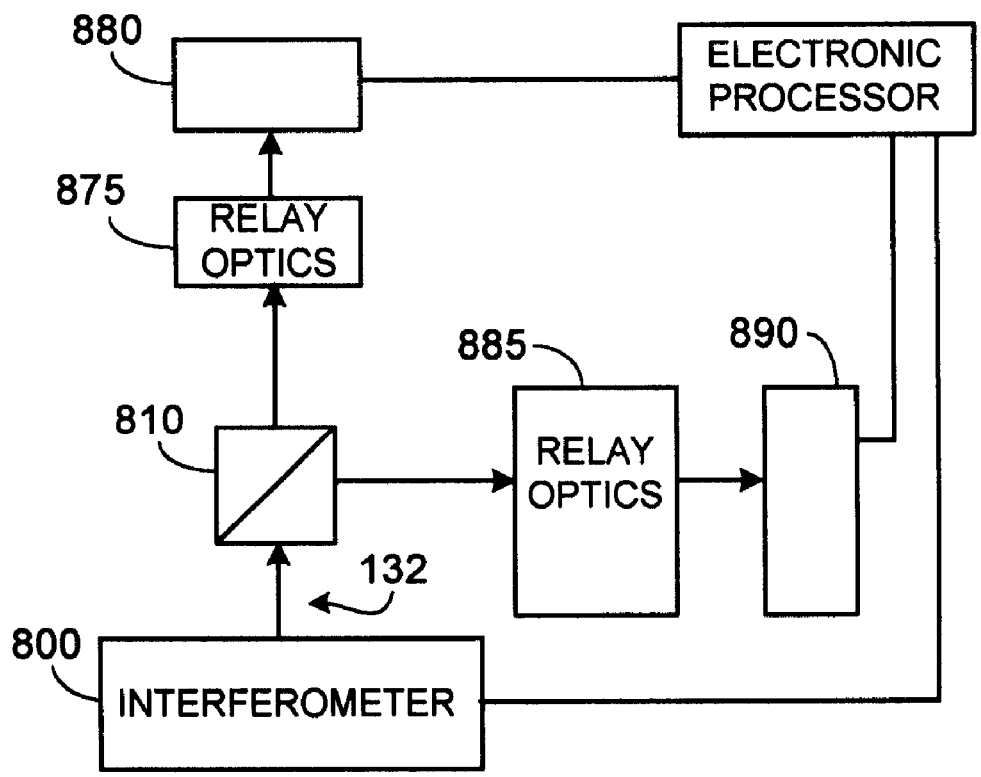
FIG. 8 is a schematic diagram of yet another embodiment for interferometry system 100.

In yet a further embodiment, shown schematically in FIG. 8, a beam splitter 810 can split the combined light 132 received from the rest of the interferometry system 800 into two channels with two corresponding multi-element detectors 880 and 890, with one channel using relay optics 875 to image pupil plane 114 to the first detector 880 to provide the ellipsometry mode measurement and the other channel using relay optics 885 to image the test surface to the second detector 890 to simultaneously provide the profiling mode measurement. Both detectors are coupled to electronic processor 870, which analyze the detector images as described above.

Various combinations of these approaches are also possible. For example, the system can include optics that image the pupil plane to a first portion of a common electronic detector and image the test surface to a second portion of the common electronic detector. In this case, the different portions of the common electronic detector can be considered to be separate detectors.

Multi-Mode Operation and Applications

Figure 9:
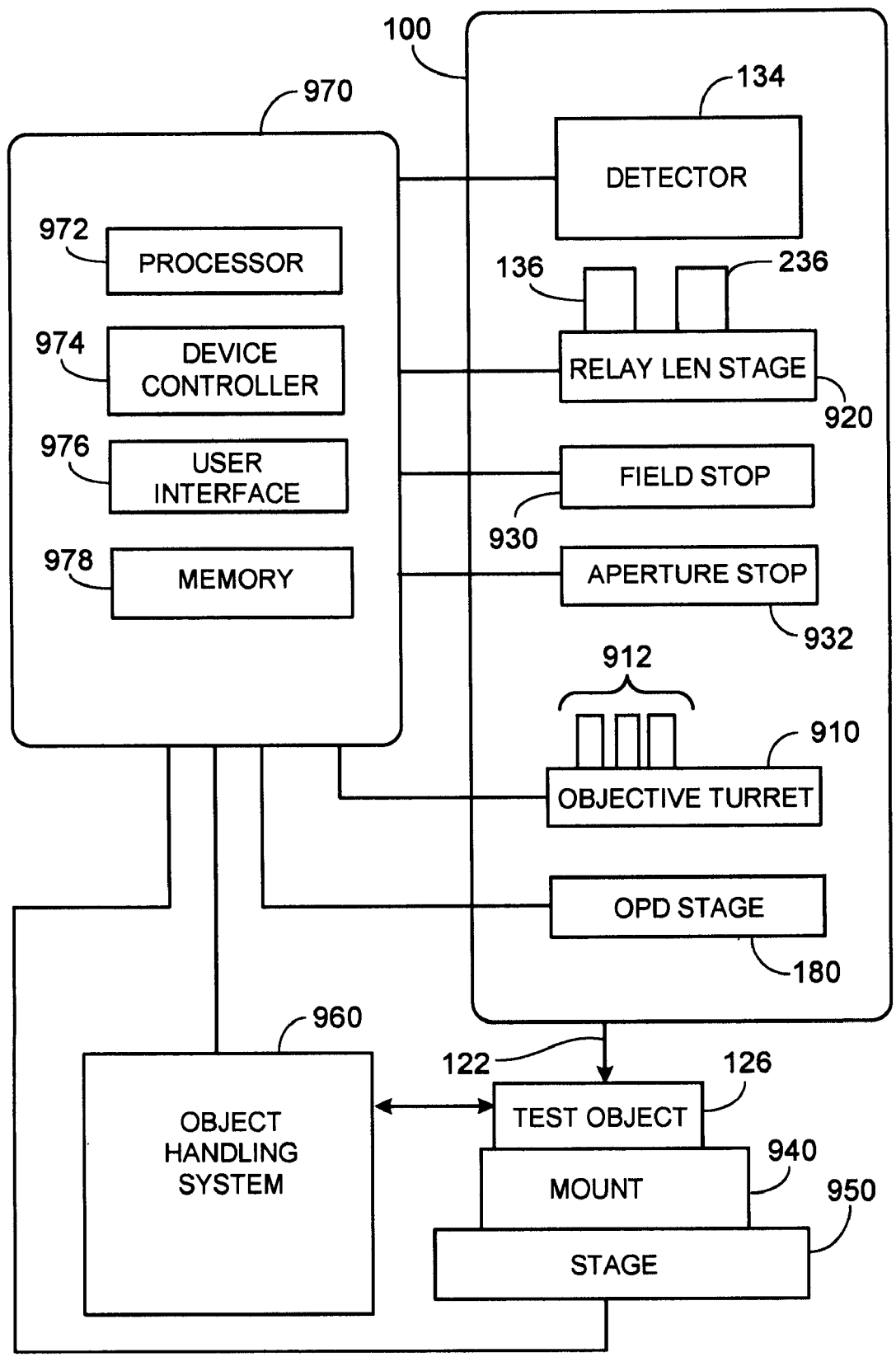
FIG. 9 is a schematic diagram of interferometry system 100 showing how various components can be adjusted in an automated fashion under the control an electronic processor.

FIG. 9 shows a schematic diagram of how various components in interferometry system 100 can be automated under the control of electronic processor 970, which, in the presently described embodiment, can include an analytical processor 972 for carrying out mathematical analyses, device controllers 974 for controlling various components in the interferometry system, a user interface 976 (e.g., a keyboard and display), and a storage medium 978 for storing calibration information, data files, a sample models, and/or automated protocols.

First, the system can include a motorized turret 910 supporting multiple objectives 912 and configured to introduce a selected objective into the path of input light 104. One or more of the objectives can be interference ovbjectives, with the different interference objectives providing different magnifications. Furthermore, in certain embodiments, one (or more) of the interference objectives can be especially configured for the ellipsometry mode of operation by having polarization element 146 (e.g., a linear polarizer) attached to it. The remaining interference objectives can be used in the profiling mode and, in certain embodiments, can omit polarization element 146 so as to increase light efficiency (such as for the embodiment described above in which beam splitter 112 is a polarizing beam splitter and polarization element is 142 is a quarter wave plate). Moreover, one or more of the objectives can be a non-interferometric objective (i.e., one without a reference leg), each with a different magnification, so that system 100 can also operate in a conventional microscope mode for collecting optical images of the test surface (in which case the relay lens is set to image of test surface to the detector). Turret 910 is under the control of electronic processor 970, which selects the desired objective according to user input or some automated protocol.

Next, the system includes a motorized stage 920 (e.g., a tube lens holder) for supporting relay lenses 136 and 236 and selectively positioning one of them in the path of combined light 132 for selecting between the first mode (e.g., an ellipsometry or reflectometry mode) in which the pupil plane 114 is imaged to the detector and the second mode (e.g., profiling or microscope mode) in which the test surface is imaged to the detector. Motorized stage 920 is under the control of electronic processor 970, which selects the desired relay lens according to user input or some automated protocol. In other embodiments, in which a translation stage is moved to adjust the position of the detector to switch between the first and second modes, the translation is under control of electronic processor. Furthermore, in those embodiments with two detection channels, each detector is coupled to the electronic processor 970 for analysis.

Furthermore, the system can include motorized apertures 930 and 932 under control of electronic processor 970 to control the dimensions of field stop 138 and aperture stop 115, respectively. Again the motorized apertures are under the control of electronic processor 970, which selects the desired settings according to user input or some automated protocol.

Also, translation stage 150, which is used to vary the relative optical path length between the test and reference legs of the interferometer, is under the control electronic processor 970. As described above, the translation stage can be coupled to adjust the position of the interference objective relative to a mount 940 for supporting test object 126. Alternatively, in further embodiments, the translation stage can adjust the position of the interferometry system as a whole relative to the mount, or the translation stage can be coupled to the mount, so it is the mount that moves to vary the optical path length difference.

Furthermore, a lateral translation stage 950, also under the control of electronic processor 970, can be coupled to the mount 940 supporting the test object to translate laterally the region of the test surface under optical inspection. In certain embodiments, translation stage 950 can also orient mount 940 (e.g., provide tip and tilt) so as to align the test surface normal to the optical axis of the interference objective.

Finally, an object handling station 960, also under control of electronic processor 970, can be coupled to mount 940 to provide automated introduction and removal of test samples into system 100 for measurement. For example, automated wafer handling systems known in the art can be used for this purpose. Furthermore, if necessary, system 100 and object handling system can be housed under vacuum or clean room conditions to minimize contamination of the test objects.

The resulting system provides great flexibility for providing various measurement modalities and procedures. For example, the system can first be configured in the microscope mode with one or more selected magnifications to obtain optical images of the test object for various lateral positions of the object. Such images can be analyzed by a user or by electronic processor 970 (using machine vision techniques) to identify certain regions (e.g., specific structures or features, landmarks, fiducial markers, defects, etc.) in the object. Based on such identification, selected regions of the sample can then be studied in the ellipsometry mode to determine sample properties (e.g., refractive index, underlying film thickness(es), material identification, etc.).

Accordingly, the electronic processor causes stage 920 to switch the relay lens to the one configured for the ellipsometry mode and further causes turret 910 to introduce a suitable interference objective into the path of the input light. To improve the accuracy of the ellipsometry measurement, the electronic processor can reduce the size of the field stop via motorized aperture 930 to isolate a small laterally homogenous region of the object. After the ellipsometry characterization is complete, electronic processor 970 can switch the instrument to the profiling mode, selecting an interference objective with a suitable magnification and adjusting the size of field stop accordingly. As described above, the profiling mode captures interference signals that allow reconstructing the topography of, for example, one or more interfaces that constitute the object. Notably, as described in greater detail below, the knowledge of the optical characteristics of the various materials determined in the ellipsometry mode allows for correcting the calculated topography for thin film or dissimilar and material effects that would otherwise distort the profile. See, for example, U.S. patent application Ser. No. 10/795,579 entitled "PROFILING COMPLEX SURFACE STRUCTURES USING SCANNING INTERFEROMETRY" and published as U.S. Patent Publication No. US-2004-0189999-A1, which was incorporated by reference above. If desired, the electronic processor can also adjust the aperture stop diameter via motorized aperture 932 to improve the measurement in any of the various modes.

When used in conjunction with automated object handling system 960, the measurement procedure can be repeated automatically for a series of samples. This could be useful for various process control schemes, such as for monitoring, testing, and/or optimizing one or more semiconductor processing steps.

For example, the system can be used in a semiconductor process for tool specific monitoring or for controlling the process flow itself. In the process monitoring application, single/multi-layer films are grown, deposited, polished, or etched away on unpatterned Si wafers (monitor wafers) by the corresponding process tool and subsequently the thickness and/or optical properties are measured using the interferometry system disclosed herein (for example, by using the ellipsometry mode, the profiling mode, or both). The average, as well as within wafer uniformity, of thickness (and/or optical properties) of these monitor wafers are used to determine whether the associated process tool is operating with targeted specification or should be retargeted, adjusted, or taken out of production use.

In the process control application, latter single/multi-layer films are grown, deposited, polished, or etched away on patterned Si, production wafers by the corresponding process tool and subsequently the thickness and/or optical properties are measured with the interferometry system disclosed herein (for example, by using the ellipsometry mode, the profiling mode, or both). Production measurements used for process control typical include a small measurement site and the ability to align the measurement tool to the sample region of interest. This site may consists of multi-layer film stack (that may itself be patterned) and thus requires complex mathematical modeling in order to extract the relevant physical parameters. Process control measurements determine the stability of the integrated process flow and determine whether the integrated processing should continue, be retargeted, redirected to other equipment, or shut down entirely.

Specifically, for example, the interferometry system disclosed herein can be used to monitor the following equipment: diffusion, rapid thermal anneal, chemical vapor deposition tools (both low pressure and high pressure), dielectric etch, chemical mechanical polishers, plasma deposition, plasma etch, lithography track, and lithography exposure tools. Additionally, the interferometry system disclosed herein can be used to control the following processes: trench and isolation, transistor formation, as well as interlayer dielectric formation (such as dual damascene).

Combining Information from Different Modes

One powerful feature of interferometry system 100 is that not only is it possible to gather rapidly and in automated fashion information about the test object for a variety of measurement modes, but also, that information determined from one mode of operation can be used to improve the accuracy of the measurement in the other mode of operation.

For example, when in the ellipsometry mode of operation, the electronic processor can determine the optical properties of various materials present at different locations on an object (for example copper lines separated by dielectric regions on a semiconductor wafer). In such cases, each material typically requires a separate measurement. Once these properties are known it is possible to calculate the phase change on the reflection (PCOR) undergone by light reflecting off the object surface. As described above in the profiling analysis section, these phase changes are material dependent and affect the topography measurement. For example, copper regions appear lower than they truly are with respect to the dielectric regions. However, the knowledge of the material dependent phase changes determined in the ellipsometry mode allows the electronic processor to correct the topography map to obtain the true surface topography. In practice, the phase change on reflection for a given angle of incidnece and wavelength affects the measured signal as a contribution to the parameter $\phi$ in Equation 20. For example, one can write:

$$\phi_{60\lambda} = \phi^{system}_{\alpha\lambda} - \phi^{part}_{\alpha\lambda} \quad (20)$$

where $\phi^{system}_{\alpha\lambda}$ is a characteristic of the instrument and $\phi^{part}_{\alpha\lambda}$ is the phase change on reflection for that particular measurement location. In the case of bulk materials such as thick metal films the surface characterization technique yields a refractive index calculated for example using Equation (6). The electronic processor can then calculate the value of the phase change of reflection for light reflecting off the metal at various angles of incidences and wavelengths using the complex argument of the Fresnel coefficients of reflection. For more complicated surface structures the optimization of the merit function in Equation (8) yields the optical properties of the structure. The scattering matrix technique then calculates the phase change of reflection as a function of angle of incidence and wavelength. As described above in the profiling analysis section, when a low numerical aperture (NA) interference objective is used for topography measurements the correction for the effect of the phase change on reflection amounts simply to subtracting from the surface height the calculated phase change divided by the wavenumber used for surface height calculation (e.g., as shown in Eq. 16). For high-NA interference objectives the correction results from the modeling of the interferometer: the model sums the interference signals generated by various source points at various wavelengths with the appropriate weights for an object point of height h=0. The sum interference signal is analyzed with the same algorithm used for topography measurement and yields an effective height h', which is simply the height offset due to the combination of phase changes on reflection. The value h' is then subtracted from the experimental topography map at the locations corresponding to the particular surface structure.

In another example, the accuracy of the measurement in the ellipsometry mode is improved when the object surface is normal to the optical axis of the interference objective (i.e., there is no tip and tilt of the object surface relative to the interference objective). This can be accomplished by having the electronic processor switch to the topography mode and performing repeated measurements of the surface tip and tilt while adjusting part orientation. As described above, the procedure can be automated with a motorized tip/tilt stage 960, which makes the instrument self aligning. Once the part is properly nulled the instrument can switch back to the surface characterization mode (e.g., an ellipsometry mode or a reflectometry mode).

In yet another example, the topography mode of measurement can also be used to measure the surface roughness of a top layer. This information can then be included in the ellipsometric model of the surface. Similarly, the topography of the top surface potentially provides information about the thickness uniformity of a film. This information can be used to best select the size of the field stop that defines the measurement area in surface characterization mode. For example, one may want to select a small region where the thickness is nominally constant.

Furthermore, in those embodiments in which a portion of the interference signal is selected to isolate a corresponding interface in the test object, it is possible to measure the film optical thickness or physical thickness (if the refractive index is known) in the topography mode. This a priori information on thickness can then be fed to the surface characterization mode and provide accurate guess values for the ellipsometry model.

Concurrent Profiling and Angularly-Resolved Measurement

Figure 10:
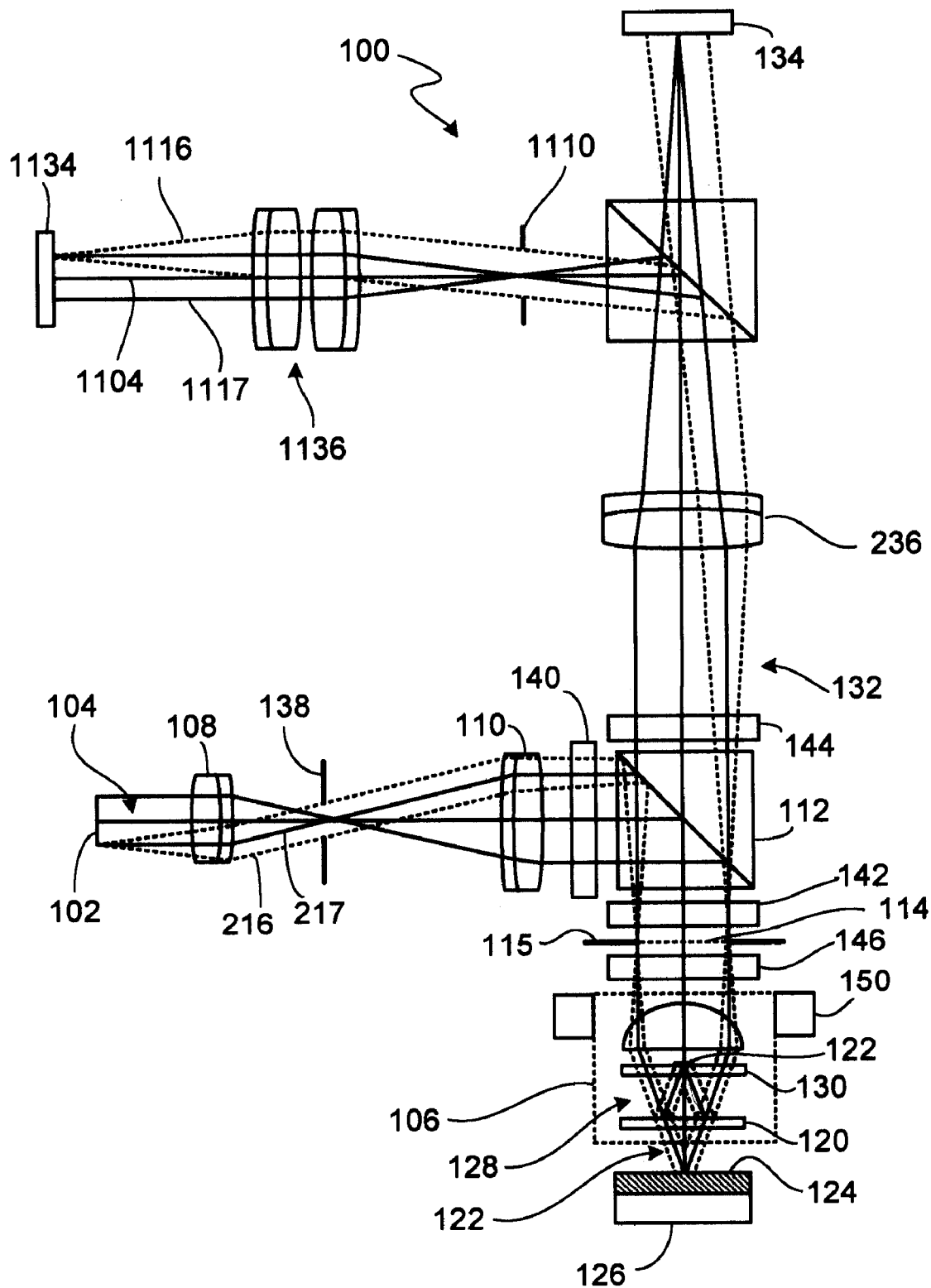
FIG. 10 is a schematic diagram of yet another embodiment for interferometry system 100.

Referring to FIG. 10, in another embodiment, system 100 in the profiling mode shown in FIG. 3 is modified to also allow concurrent angularly resolve (e.g. reflectometry or ellipsometry) measurement. As described above, lens 236 is placed such that the points on surface 124 are imaged to corresponding points on detector 134 (as indicated by marginal rays 216 and chief rays 217 from source 102), thereby allowing a surface profiling measurement to determine, for example, a topography measurement.

In order to allow a concurrent, angularly resolved measurement, beam splitter 1101 is placed between lens 236 and detector 134 to divert a portion of combined light 132 to form a second beam 1104. Beam 1104 is directed to field stop 1110 and on through relay lens 1136 to form an optical interference pattern on electronic detector 1134 (as indicated by chief rays 1117 and marginal rays 1116). The intensity profile of the optical interference pattern across the detector is measured by different elements of the detector and stored in an electronic processor (not shown) for analysis. Pupil plane 114 is imaged onto the detector by relay lens 1136 such that different points on the pupil plane 114 are imaged to corresponding points on detector 1134.

As described above, because each source point illuminating pupil plane 114 creates a plane wave front for test light 122 illuminating test surface 124, the radial location of the source point in pupil plane 114 defines the angle of incidence of this illumination bundle with respect to the object normal. Thus, all source points located at a given distance from the optical axis correspond to a fixed angle of incidence, by which objective lens 118 focuses test light 122 to test surface 124. After reflection from the test and reference surfaces, combined light 132 forms a secondary image of the source at pupil plane 114 of the objective lens. Because the portion of combined light diverted to form beam 1104 is then re-imaged by relay lens 1136 onto detector 1134, the different elements of the detector 1134 correspond to the different illumination angles of test light 122 on test surface 124.

Field stop 1110 positioned between beam splitter 1101 restricts the portion of beam 1104 incident on detector 1134, in turn restricting the extent of the object surface used to collect angularly resolved data. For example, field stop 1110 can be a fixed aperture, a series of user-selectable physical apertures or a user-programmable aperture such as that created using a spatial light modulator (for example a pixelated LCD filter). It is possible to create effective apertures with arbitrary shapes. It is also possible to locate an effective aperture which restricts the measurement to any arbitrary location on the object surface within the field of view of the optics.

Accordingly, interferometry system 100 operates to acquire angularly resolved information about an area or areas of the surface of object 126 using detector 1134 while concurrently obtaining surface profile information using detector 134. For example, both an ellipsometry/reflectometry measurement and a surface profile measurement may be acquired during a single scan of interference objective 106.

Information from concurrent measurements can be combined to supplement, confirm, or improve the other. For instance, where field stop 1101 is selectable/programmable, a first aperture can be created at a location A. An angularly resolved measurement then provides the optical properties of the object at that location. Using, for example, the techniques described above, the procedure is repeated at a location B. The measured optical property information can then be used to improve a concurrent profile measurement. For example, using the measured optical property information, it is possible to calculate the height offset that would be reported in a concurrently measured profile map covering locations A and B due to the difference in optical properties. Such optical effects in the profile map are reduced by correcting for the calculated height offsets, resulting in a corrected topography map.

Concurrent measurement increases the through-put of interferometry system 100 by decreasing the number of separate measurements, each of them time consuming. Increased throughput is desirable in many applications. For example, interferometry system 100 can provide semiconductor wafer metrology in an integrated circuit production line. Increased throughput can insure that the system does not become a bottleneck which slows the entire line.

Narrow-band Tunable Source

In yet another embodiment, light source 102 in system 100 of FIG. 1 is replaced by a tunable monochromatic source under the control of the electronic processor. For example, the source can be a tunable laser diode or a broadband source incorporating a tunable spectral filter to produce a tunable spectral output (e.g., a monochromator, a spectral filter wheel, or a tunable liquid crystal filter). Furthermore, the position of reference mirror 122 is adjusted so that the optical path length difference between the test light and reference light when the test surface is in-focus with respect to the interference objective is non-zero. Detector 134 records the interference pattern produced by the combined light as the wavelength of the source is scanned. There is no mechanical motion of the object with respect to the interferometric objective in this case. Because of the adjustment in the position of the reference mirror and the resulting non-zero optical path length difference between the test and reference legs of the interferometer, the scanning of the source frequency produces an interference signal that is measured at each detector element. This interference signal is sometimes referred to as a "channel spectrum."

When operating in the ellipsometry mode (as in FIG. 1), the intensity of the interference signal measured at each detector element corresponds to Eq. 4, except that "z" is fixed at the non-zero optical path length difference, and the wavenumber k is varied. During analysis, the electronic processor determines the wavelength-dependent, complex reflectivity of the test surface from the interference cross-term in Eq. 4 using an analytical framework similar to that shown above. For example, the interference signal at each detector element can be Fourier transformed, filtered to select the portion of the transformed signal corresponding to the cross-term, and then inversed Fourier transformed to give the magnitude and phase of the signal with respect to wavelength. This magnitude and phase can then be related as to ellipsometry parameters in a similar fashion to that described above. When operating in the profiling mode (as in FIG. 3), the interference signal in the present embodiment can be Fourier transformed, and variations in the phase at the non-zero optical path length difference coordinate in the transform over the various detector elements can be related changes in the topography of the test surface. Information from the other coordinates in the Fourier transform can also be analyzed to provide topography information.

Accordingly, this narrow-band, tunable source embodiment can also operate in the various modes of operation and for the various applications described above.

Broadband Spatially Coherent Illumination

In some embodiments, the test object is illuminated with spatially coherent light. Light is said to be spatially coherent when the oscillation of the electromagnetic field is substantially correlated (i.e., has a substantially fixed phase relationship) for points spatially separated in a direction transverse to the direction of propagation. See *Encylcopedia of Laser Physics and Technology*, available at http://www.rp-photonics.com/coherence.html and E. Hecht, *Optics, Second Edition*, pp. 516-517, Addison Wesley, 1987. For example, in a spatially coherent light beam, the electromagnetic field at points on a cross-section of the beam will oscillate in a correlated way. As will be described below, the use of spatially coherent light allows for diffraction limited or near-diffraction limited illumination of areas on the test object. In certain embodiments, this allows for illumination and measurement of small, well-defined regions of the test surface. Further, in some embodiments, the spatially coherent illuminating light can be spectrally broadband, allowing for wavelength resolved measurements, as described above.

Figure 11:
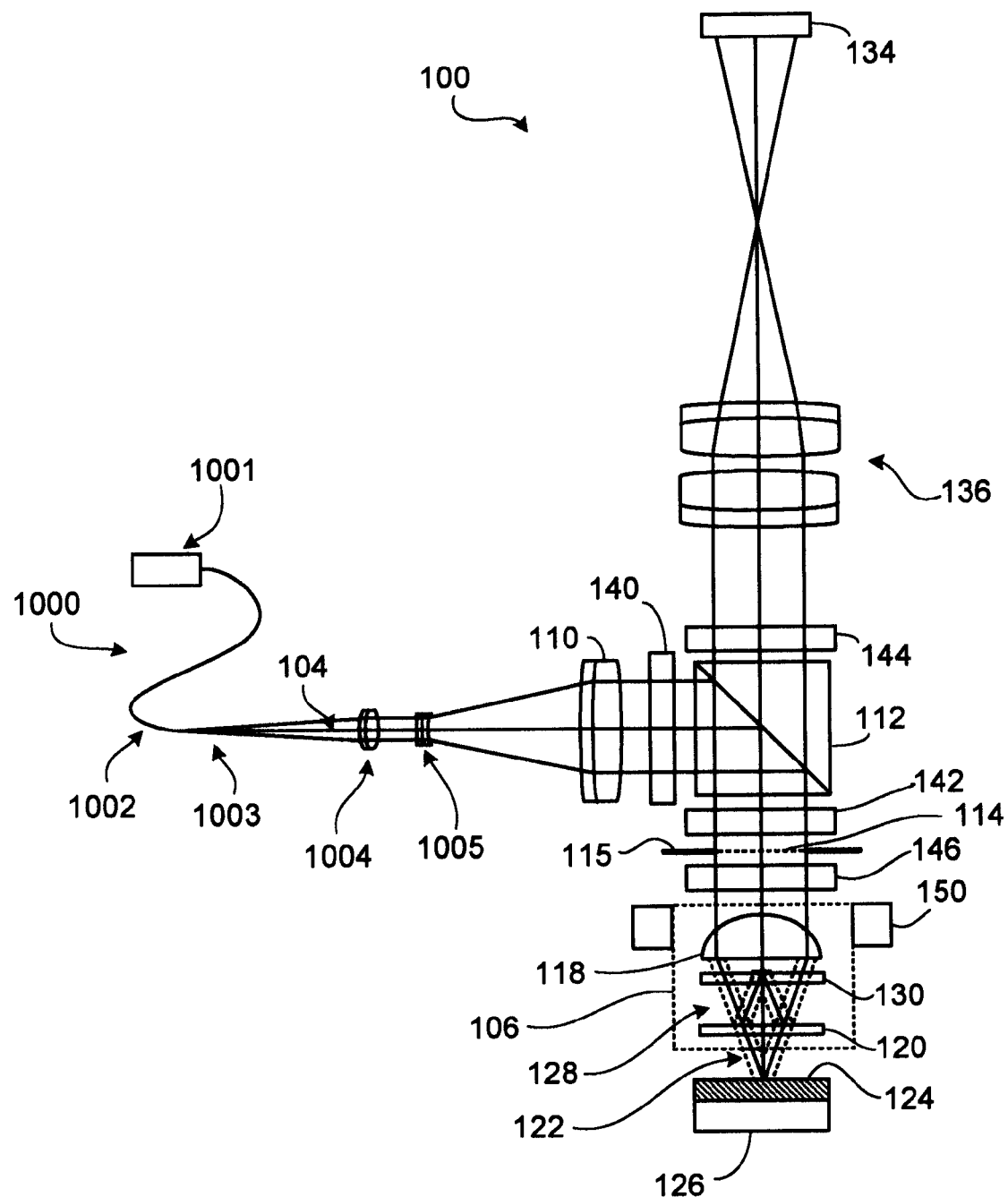
FIG. 11 is a schematic diagram of interferometry system 100 configured to operate in an ellipsometry mode, featuring broadband, spatially coherent illumination.

For example, referring to FIG. 11, interferometer system 100 operates in an ellipsometry mode, as shown in FIG. 1, but with a broadband spatially coherent illumination system 1000 (described in more detail below), replacing elements 102, 108, and 138. In the present embodiment, light source 1001 is coupled to optical fiber 1002 to generate spatially coherent input light 104 (the chief rays of which are indicated by solid lines). Input light 104 is spatially coherent across face 1003 of fiber 1002. As indicated by chief rays, input light 104 is collimated by collimator lens 1004. The collimated beam is expanded by expander lens 1005 to match the size of objective pupil aperture stop 115, re-collimated by lens 110, and directed to pupil plane 114 of interference objective 106. For example, in embodiments where shape of the light beam is Gaussian (or nominally Gaussian) the beam waist may be imaged pupil plane 114.

Beam splitter 120 separated input light 104 into test light 122, which is directed to a test surface 124 of a test object 126, and reference light 128, which reflects from reference surface 122. Objective lens 118 focuses the test and reference light to the test and reference surfaces, respectively. The reference optic 130 supporting reference surface 122 is coated to be reflective only for the focused reference light, so that the majority of the input light passes through the reference optic before being split by beam splitter 120.

After reflecting from the test and reference surfaces, the test and reference light are recombined by beam splitter 120 to form combined light 132, which is transmitted by beam splitter 112 and relay lens 136 to form an optical interference pattern on an electronic detector 134. The intensity profile of the optical interference pattern across the detector is measured by different elements of the detector and stored in an electronic processor (not shown) for analysis. In this ellipsometry configuration, the pupil plane 114 is imaged onto the detector. In the present embodiment, relay lens 136 images different points on the pupil plane 114 to corresponding points on detector 134.

Illumination system 1000 provides spatially coherent illumination over a broad band of wavelengths (e.g., an emission spectrum having a full-width, half-maximum of more than 50 nm, or preferably, even more than 100 nm). Such broadband, spatially coherent illumination can be provided by a number of types of sources.

For example, in some embodiments, optical fiber 1002 is a so called "monomode" fiber. A monomode fiber supports only a single (or, in some cases, a few) spatial mode for light propagating along the fiber. See, e.g., *Encyclopedia of Laser Physics and Technology*, available at http://www.rp-photonics.com/single_mode_fibers.html. Thus, when light source 1001 is coupled to the fiber, output light 104 contains primarily light in the supported spatial mode. The light across output face 1003 is thereby well correlated, yielding spatially coherent output light 104. Monomode fibers are typically capable of supporting a single spatial mode over a range of wavelengths. Thus, when light source 1001 is a broadband source (e.g. a broadband or "white light" LED, an LED array, a pulsed or broadband laser source, etc) which inputs light over a spectral range within the range of supportable wavelengths, the light output by monomode fiber 1002, will be both broadband and spatially coherent In some embodiments, the optical fiber 1002 includes a photonic bandgap material (e.g. photonic crystal material) or other nonlinear material which is capable of supporting spatially coherent light over a very broad range of wavelengths (e.g. up to hundreds of nanometers or more), thereby allowing for very broadband spatially coherent illumination. See, e.g. *Encyclopedia of Laser Physics and Technology*, available at http://www.rp-photonics.com/photonic_crystal_fibers.html. Such systems are sometimes said to provide "supercontinuum" illumination. In some such embodiments, fiber 1002 may also be a monomode fiber, supporting a single (or few) spatial mode for light over a very wide range of wavelengths (e.g. a range spanning wavelengths from the infra-red and above to the ultraviolet and below). See, e.g. *Encyclopedia of Laser Physics and Technology*, available at http://www.rp-photonics.com/supercontinuum_generation.html.

In some embodiments, fiber 1002 contains nonlinear material which acts to further broaden the spectral range of light input into the fiber. Nonlinear effects (e.g. Raman scattering or four wave mixing) occur as the light propagates along the fiber, producing light at wavelengths other than those present in the input light. In some such embodiments, light source 1001 may be a relatively narrowband source, with spectral broadening provided by fiber 1002 to produce broadband output light 104.

In further embodiments, illumination system 1000 includes a resonant cavity capable of producing a spatially coherent output beam. For example, light source 1001 may include a resonant cavity pumped by a source (e.g. a laser, LED, or LED array) to excite the cavity to resonate at a single (or a few) spatial mode of the cavity. The output of the cavity will thereby be spatially coherent. In some such embodiments, fiber 1002 may be removed, with input light 104 deriving directly from light source 1001 (e.g., as the output beam of the resonant cavity). In some embodiments the cavity may include a filter which acts to limit the number of spatial modes which are supported by the resonant cavity.

Note that coherent illumination differs from cases in which the measurement object is illuminated by light with a low degree of spatial coherence (e.g., when using a spatially incoherent extended source imaged at pupil plane 114 to provide Koehler illumination). For example, in typical applications (e.g. those where some minimum intensity is required at the detector for a useful measurement), a spatially incoherent illuminating light beam will produce a large spot size at test object 126 (e.g., a spot size significantly wider than the diffraction spot of interference objective 106).

In the present embodiment, however, test light 122 is spatially coherent, and may be focused to a small spot size at test object 126. The focused beam at test object 126 is, in this case, the convolution of the geometrical point spread function of interference objective 106 by its diffraction spot. For spatially coherent pupil plane illumination, the geometrical point spread is defined as the irradiance distribution at the object of point sources in pupil plane 114, when all diffraction effects are ignored. In typical embodiments, the geometric point spread of interference objective 106 depends on, for example, optical aberrations in the objective, and can be reduced or even eliminated using correction techniques know in the art. The diffraction spot is, on the other hand, the irradiance distribution at object 126 due to diffraction effects including, for example, effects of apertures, obscurations, etc along the objective.

For a well corrected objective illuminated with spatially coherent light, the spot size at test object 126 can approach or essentially equal the width of the diffraction spot at the test object. For an objective with a high numerical aperture objective (e.g., about 0.7 or greater, or about 0.9 or greater), the diffraction spot can be, for example, a fraction of a micrometer for the central lobe of the illumination spot. Thus, in the presently described embodiment and using the techniques described above, interferometry system 100, in an ellipsometry mode, can determine angle, wavelength, and polarization resolved information (e.g. complex reflectance information) for a small, well defined region of test surface 124 of test object 126. Such a measurement can be repeated over multiple areas on test surface 124. For example, complex reflectance measurements taken at multiple test spots across test surface 124 can be analyzed to map out properties of test object 126 such as film thickness, material type, index of refraction etc. Such information could, for example, be used to improve a surface profile measurement made using interferometry system 100 operating in a profiling mode.

Note that spatially coherent illumination differs from illumination by light with a low degree of spatial coherence in another respect. For spatially incoherent light, light diffusely reflected from test surface 124 will combine incoherently (e.g. with a random phase relationship) at detector 134. Thus, over a few periods, the intensity of the combined electromagnetic field at detector 134 corresponding to the diffusely reflected light will average to zero. As typical detection times are generally much longer than a few periods, the diffusely reflected light will therefore have no contribution to the interference signal measured by detector 134.

This is not the case for spatially coherent illumination. Instead, diffusely reflected light will combine coherently at detector 134. The intensity of the diffusely reflected light will therefore not average to zero, and so may contribute to the interference signal measured by detector 134. In some applications, (e.g. when the test surface does not have substantial lateral variations across the measurement spot) this contribution will be negligible. In such cases, the measurement model of Eq. 3 remains a good approximation, allowing the use of the analysis techniques described above. In cases where the contribution due to diffuse reflection to the measured interference signal is significant, Eq. 3 is no longer a good approximation. However, such signals may still be analyzed using, for example, model based techniques in which the measured signal is compared to, for example, model signals calculated using the full Maxwell's equations and/or exemplary signals based on known reference samples. Examples of such techniques are be found in U.S. Provisional Patent Application No. 60/876,748, entitled APPARATUS AND METHOD FOR MEASURING CHARACTERISTICS OF SURFACE FEATURES and filed on Dec. 22, 2006, which is incorporated herein by reference.

In some embodiments, interferometry system 100 includes an optical element (e.g. a diffuser) which may be selectively switched into the beam path to reduce the spatial coherence of the illuminating light. In some applications it is desirable to switch between spatially coherent illumination which illuminates a larger portion of test object. In some cases (e.g. when measuring a slightly rough or patterned object), a larger measurement spot may be useful to improve the statistics of the measurement. For example one may provide the option of Koehler illumination by imaging the spatially coherent light source (i.e. fiber face 1003) onto a diffuser (not shown) placed within aperture stop 115 of interference objective 106.

Although the presently described embodiment describes the use of broadband spatially coherent illumination source with interferometry system 100 in an ellipsometry mode, it is to be understood that such a source can be used similarly in a variety of other modes, including the profiling mode described above.

Additional Embodiments

The embodiments shown in FIGS. 1 and 3 implement an interference objective of the Mirau-type, in which the beam splitter in the interference objective directs the reference light back along the optical axis for the test light. In other embodiments, interferometry system 100 can instead use a different type of interference objective, such as a Michelson objective, in which the beam splitter directs the reference light away from the optical axis of the test light (e.g., the beam splitter can be oriented at 45 degrees to the input light so the test light and reference travel at right angles to one another). In such cases, the reference surface can be positioned outside of the path of the test light.

In another embodiment, the interference objective can be of the Linnik-type, in which the case the beam splitter is positioned prior to the objective lens for the test surface (with respect to the input light) and directs the test and reference light along different paths. A separate objective lens is used to focus the reference light to the reference lens. In other words, the beam splitter separates the input light into the test and reference light, and separate objective lenses then focus the test and reference light to the respective test and reference surfaces. Ideally the two objective lenses are matched to one another so that the test and reference light have similar aberrations and optical paths.

Additional interferometer configurations are also possible. For example, the system can be configured to collect test light that is transmitted through the test sample and then subsequently combined with reference light. For such embodiments, for example, the system can implement a Mach-Zehnder interferometer with dual microscope objectives on each leg.

The light source in the interferometer may be any of: an incandescent source, such as a halogen bulb or metal halide lamp, with or without spectral bandpass filters; a broadband laser diode; a light-emitting diode; a combination of several light sources of the same or different types; an arc lamp; any source in the visible spectral region; any source in the IR spectral region, particularly for viewing rough surfaces & applying phase profiling; and any source in the UV spectral region, particularly for enhanced lateral resolution. For broadband applications, the source preferably has a net spectral bandwidth broader than 5% of the mean wavelength, or more preferably greater than 10%, 20%, 30%, or even 50% of the mean wavelength. For tunable, narrow-band applications, the tuning range is preferably broad (e.g., greater than 50 nm, greater than 100 nm, or greater than even 200 nm, for visible light) to provide reflectivity information over a wide range of wavelengths, whereas the spectral width at any particular setting is preferable narrow, to optimize resolution, for example, as small as 10 nm, 2 nm, or 1 nm. The source may also include one or more diffuser elements to increase the spatial extent of the input light being emitted from the source.

In some embodiments the interferometer can be configured such that some or all of the interferometer's optical elements are reflective elements. For example, in applications where input light is in the UV or extreme UV (EUV) spectral, refractive optical elements using typical materials would absorb a substantial amount of the light. In such applications all refractive elements in the interferometer could be replaced by reflective elements such as, for example, curved mirrors.

Furthermore, the various translations stages in the system, such as translation stage 150, may be: driven by any of a piezo-electric device, a stepper motor, and a voice coil; implemented opto-mechanically or opto-electronically rather than by pure translation (e.g., by using any of liquid crystals, electro-optic effects, strained fibers, and rotating waveplates) to introduce an optical path length variation; any of a driver with a flexure mount and any driver with a mechanical stage, e.g. roller bearings or air bearings.

The electronic detector can be any type of detector for measuring an optical interference pattern with spatial resolution, such as a multi-element CCD or CMOS detector.

In various embodiments, interferometer system 100 outputs measurement information to, for example, a user display, a printer, a machine-readable medium or storage device, a electronic controller, etc. In some embodiments, the output data can automatically control a further device or devices (e.g., integrated circuit processing and/or metrology tools).

Software

The analysis steps described above can be implemented in computer programs using standard programming techniques. Such programs are designed to execute on programmable computers or specifically designed integrated circuits, each comprising an electronic processor, a data storage system (including memory and/or storage elements), at least one input device, and least one output device, such as display or printer. The program code is applied to input data (e.g., images from the detector) to perform the functions described herein and generate output information (e.g., refractive index information, thickness measurement(s), surface profile(s), etc.), which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis and control functions described herein.

A number of embodiments of the invention have been described. Nevertheless, it will be understood that various modifications may be made without departing from the spirit and scope of the invention.

What is claimed is:

1. An apparatus comprising:
   an interferometer configured to direct broadband spatially coherent test light to a test surface of a test object over a range of illumination angles and subsequently combine it with reference light to form an interference pattern, the test and reference light being derived from a common source;
   a multi-element detector; and
   one or more optics configured to direct at least a portion of the combined light to the detector so that different elements of the detector correspond to different illumination angles of a region of the test surface illuminated by the test light.

2. The apparatus of claim 1, further comprising the common source, wherein the common source is a broadband spatially coherent source.

3. The apparatus of claim 2, wherein the common source is a broadband source spanning more than 50 nm at full width half maximum.

4. The apparatus of claim 3, wherein the common source is a broadband source spanning more than 100 nm at full width half maximum.

5. The apparatus of claim 4, wherein the common source is a broadband source spanning more than 500 nm at full width half maximum.

6. The apparatus of claim 5, wherein the common source is a broadband source spanning more than 1000 nm at full width half maximum.

7. The apparatus of claim 3, wherein the interferometer comprises an interference objective having a pupil plane, and wherein the one or more optics image the interference pattern at the pupil plane to the multi-element detector.

8. The apparatus of claim 7, wherein input light is directed from the common source to the pupil plane.

9. The apparatus of claim 8, wherein the input light directed to the pupil plane is spatially coherent at the pupil plane.

10. The apparatus of claim 7, wherein the common source outputs a beam having a waist, and wherein the waist of the beam is imaged to the pupil plain.

11. The apparatus of claim 9, further comprising a field stop positioned to define the spatial extent of the test light on the test surface.

12. The apparatus of claim 9, wherein the interference objective is configured to focus the test light to a test spot at the test surface.

13. The apparatus of claim 12, wherein the width of the test spot is about equal to the width of a diffraction spot of the interference objective at the test surface.

14. The apparatus of claim 13, wherein the width of the test spot is about 150% or less of the width of a diffraction spot of the interference objective.

15. The apparatus of claim 13, wherein the width of the test spot is about 200% or less of the width of a diffraction spot of the interference objective.

16. The apparatus of claim 13, wherein the numerical aperture of the of the interference objective is greater than 0.7.

17. The apparatus of claim 13, wherein the numerical aperture of the of the interference objective is greater than 0.9.

18. The apparatus of claim 16, wherein the width of the test spot is about 1 μm or less.

19. The apparatus of claim 16, wherein the width of the test spot is about 0.5 μm or less.

20. The apparatus of claim 3, wherein the common source comprises a light source optically coupled to an optical fiber configured to provide spatially coherent output light.

21. The apparatus of claim 20, wherein the light source comprises one or more of: a lamp element, a laser, a light emitting diode, a light emitting diode array.

22. The apparatus of claim 20, wherein the optical fiber comprises a single mode fiber.

23. The apparatus of claim 20, wherein the optical fiber comprises a photonic bandgap fiber.

24. The apparatus of claim 20, wherein the optical fiber comprises an optically nonlinear material.

25. The apparatus of claim 24, wherein, during operation, the fiber interacts with light from the light source propagating along the fiber to provide output light with a broader spectral range than the light source.

26. The apparatus of claim 3, wherein the common source comprises a resonant cavity configured to provide spatially coherent output light.

27. The apparatus of claim 3, further comprising an optical element configured to operate selectively to reduce the spatial coherence of the test light.

28. The apparatus of claim 3, further comprising an electronic processor coupled to the detector, wherein the electronic processor is configured to process information measured by the detector to determine information about the test object.

29. The apparatus of claim 28, wherein the test object comprises one or more layers on a substrate.

30. The apparatus of claim 28, wherein the electronic processor extracts angularly resolved reflectivity information about the test surface from the detector measurement, and determines the information about the test object based on the angularly resolved information.

31. The apparatus of claim 30, further comprising a translation stage configured to adjust the relative optical path length between the test and reference light when they form the interference pattern, wherein the electronic processor is configured to analyze an interference intensity signal measured at each of multiple locations across the detector and produced by scanning the translation stage.

32. The apparatus of claim 31, wherein the electronic processor is configured, in a first mode, to determine the correspondence between the different regions of the detector and the different illumination angles of the test surface by the test light based on the frequency of the intensity signal at different locations on the detector.

33. The apparatus of claim 32, wherein the electronic processor is configured, in the first mode, to extract angularly resolved and wavelength-resolved information about the test surface based on the intensity signals measured across the detector.

34. The apparatus of claim 33, wherein the electronic processor is configured to determine the information about the test object based on a comparison between data based on the information measured by the detector and a model for the test object.

35. The apparatus of claim 34, wherein the model provides an estimate for the measured information as a function of one or more parameters for the test object, and wherein the comparison selects values for the one or more parameters to optimize the fit between the measured information and that provided by the model.

36. The apparatus of claim 31, wherein the electronic processor stores calibration information about the optical properties of the interferometer and uses the calibration information and the information measured by the detector to determine the information about the test object.

37. The apparatus of claim 31, wherein the translation stage is configured to vary the optical path length over a range larger than a coherence length for the common source.

38. The apparatus of claim 32, wherein the one or more optics are further configured to direct at least a portion of the combined light to the detector so that different elements of the detector correspond to different locations on the region of the test surface illuminated by the test light.

39. The apparatus of claim 38, wherein the electronic processor is configured, in a second mode, to process information measured by the different elements of the detector corresponding to different locations on the region of the test surface illuminated by the test light to determine information about a test object having the test surface.

40. The apparatus of claim 39, wherein the electronic processor is configured to use information derived in one mode of operation to assist in determining further information about the test object when using another mode of operation.

41. A method comprising
directing broadband spatially coherent test light to a test surface of a test object over a range of illumination angles and subsequently combining it with reference light to form an interference pattern, the test and reference light being derived from a common source;
directing at least a portion of the combined light to a multi-element detector so that different elements of the detector correspond to different illumination angles of a region of the test surface illuminated by the test light.

42. The method of claim 41, wherein the common source is a broadband spatially coherent source.

43. The method of claim 42, wherein the common source is a broadband source spanning more than 50 nm at full width half maximum.

44. The method of claim 43, wherein the directing spatially coherent test light to the test surface comprises using an optical system to direct the test light to illuminate a test spot on the surface, wherein the width of the test spot at the test surface is about equal to a diffraction spot of the optical system at the test surface.

45. The method of claim 44, further comprising processing angularly resolved information measured by the detector to determine information about the test object.

46. The method of claim 45, further comprising:
adjusting the relative optical path length between the test and reference light when they form the interference pattern; and
analyzing an interference intensity signal measured at each of multiple locations across the detector and produced by adjusting the relative optical path length.

47. The method of claim 46, wherein the adjusting the relative optical path length comprises varying the optical path length over a range larger than a coherence length for the common source.

* * * * *

UNITED STATES PATENT AND TRADEMARK OFFICE
CERTIFICATE OF CORRECTION

| | | |
|---|---|---|
| PATENT NO. | : 7,884,947 B2 | Page 1 of 1 |
| APPLICATION NO. | : 11/758252 | |
| DATED | : February 8, 2011 | |
| INVENTOR(S) | : Xavier Colonna De Lega | |

It is certified that error appears in the above-identified patent and that said Letters Patent is hereby corrected as shown below:

Title page, column 2, item [57] Abstract, line 6 delete "source; and" and insert --source; a--.

Column 1, line 23, after "is" delete "in".

Column 32, claim 16 line 41, delete second occurrence of "of the".

Column 32, claim 17 line 43, delete second occurrence of "of the".

Signed and Sealed this
Third Day of May, 2011

David J. Kappos
*Director of the United States Patent and Trademark Office*